(12) United States Patent
Brown

(10) Patent No.: US 8,440,181 B2
(45) Date of Patent: May 14, 2013

(54) PREVENTION OF MICRONUTRIENT DEFICIENCIES ASSOCIATED WITH COMMON DISABILITIES IN THE OVER 50 ADULT

(76) Inventor: Ralph Brown, Southlake, TX (US)

( * ) Notice: Subject to any disclaimer, the term of this patent is extended or adjusted under 35 U.S.C. 154(b) by 736 days.

(21) Appl. No.: 12/366,700

(22) Filed: Feb. 6, 2009

(65) Prior Publication Data

US 2009/0220477 A1 Sep. 3, 2009

Related U.S. Application Data

(60) Provisional application No. 61/026,888, filed on Feb. 7, 2008.

(51) Int. Cl.
*A61K 38/43* (2006.01)
(52) U.S. Cl.
USPC .......................................................... 424/94.1
(58) Field of Classification Search .................. None
See application file for complete search history.

(56) References Cited

U.S. PATENT DOCUMENTS

2004/0197430 A1* 10/2004 Meyrowitz .................... 424/756

FOREIGN PATENT DOCUMENTS

WO    WO 0212882 A2 *  2/2002

OTHER PUBLICATIONS

Wholesale Nutritional Ingredients, "Multivitamin and Mineral Formula" and "Multinutrient, hypoallergenic, life extension capsules". Internet Archive Date: Mar. 19, 2006 [Retrieved from the Internet on: Oct. 29, 2011]. Retrieved from the Internet: <URL: http://web.archive.org/web/20060319093236/http://www.nutri.com/wn/ingrd.html>.*
Copper Fact Sheet, updated Jul. 28, 2007 (5 pages).
Ravaglia et al., "Homocysteine and Cognitive Function in Healthy Elderly Community Dwellers in Italy", Am J Clin Nutr., 2003; 77 (3): 668-673.
Higdon, "Carotenoids (Alpha-Carotene, Beta-Carotene, Beta-Cryptoxanthin, Lycopene, Lutein and Zeaxanthin)", Linus Pauling Institute, 2004-2005, updated Dec. 21, 2005 (29 pages).
Higdon, "Sodium (Chloride)", Linus Pauling Institute, updated Dec. 2007 (18 pages).
Higdon, "Chromium", Linus Pauling Institute, updated Jun. 2007 (14 pages).
Higdon, "Copper ", Linus Pauling Institute, updated Jul. 2007 (16 pages).
Higdon, "Folic Acid", Linus Pauling Institute, updated May 2007 (18 pages).
Higdon , "Pantothenic Acid", Linus Pauling Institute, updated May 26, 2004 (8 pages).
Higdon et al., "Phosphorus", Linus Pauling Institute, updated Aug. 2007 (9 pages).
Higdon et al., "Riboflavin", The Linus Pauling Institute, updated Jun. 2007 (12 pages).
Higdon, "Selenium", Linus Pauling Institute, updated Oct. 15, 2003 (24 pages).
Higdon, "Thiamin", Linus Pauling Institute, updated Sep. 23, 2002 (15 pages).
Higdon, "Vitamin B6", Linus Pauling Institute, updated Nov. 2007 (17 pages).
Higdon, "Vitamin B12", Linus Pauling Institute, updated Jun. 2007 (23 pages).
"Vitamin B12" (www.mayoclinic.com/health/vitamin-B12/NS_patient-vitaminb12), Natural Standard® Patient Monograph, 2007 The Natural Standard Research Collaboration (13 pages).
Higdon, "Vitamin D", Linus Pauling Institute, updated Jun. 2007 (24 pages).
Higdon, "Vitamin E", Linus Pauling Institute, updated Nov. 11, 2004 (23 pages).
Higdon, "Vitamin K", Linus Pauling Institute, 2000-2004, updated May 25, 2004 (15 pages).
Higdon, "Zinc", Linus Pauling Institute, updated Dec. 16, 2003 (18 pages).
Riboflavin, Dietary Reference Intakes for Thiamin, Riboflavin, Niacin, Vitamin B6, Folate, Vitamin B 12, Pantotenic Acid, Biotin, and Choline, National Academy Press, 1998 (36 pages).
Magnesium, Dietary Reference Intakes for Calcium, Phosphorus, Magnesium, Vitamin D, and Fluoride, National Academy Press, 1997 (61 pages).
Vitamin B6, Dietary Reference Intakes for Thiamin, Riboflavib, Niacin, Vitamin B6, Folate, Vitamin B12, Pantothenic Acid, Biotin, and Choline, National Academy Press, 1998 (46 pages).
Duffy et al., "Treatment of Hypertension with Ascorbic Acid", Lancet, 1999; 354 (9195): 2048-2049 (Abstract).
Dawson-Hughes et al., "Effect of Calcium and Vitamin D Supplementation on Bone Density in Men and Women 65 years of Age or Older" N. Engl J Med, 1997; 337 (10):670-676.
Doshi et al., "Lowering Blood Homocysteine With Folic Acid Based Supplements: Meta-Analysis of Randomised Trials. Homocysteine Lowering Trialists' Collaboration" BMJ, 1998; 316 (7135): 894-898 (Abstract).
Trivedi et al., "Effect of Four Monthly Oral Vitamin D3 (Cholecalciferol) Supplementation on Fractures and Mortality in Men and Women Living in the Community: Randomised Double Blind Controlled Trial" BMJ, 2003; 326 (7387):469-474.
Deluca, "Overview of General Physiologic Features and Functions of Vitamin D" Am J Clin Nutr., 2004; 80 (6 Suppl): 1689S-1696S.
Allain et al., "Hypovitaminosis D in Older Adults" Gerontology, 2003; 49 (5): 273-278 (Abstract).
Fortes et al., "The Effect of Zinc and Vitamin A Supplementation on Immune Response in an Older Population" J Am Geriatr Soc., 1998; 46 (1): 19-26 (Abstract).
Ryder et al., "Magnesium Intake from Food and Supplements in Associated with Bone Mineral Density in Healthy Older White Subjects" J Am Geriatr Soc., 2005; 53 (11): 1875-1880. (Abstract and Introduction).
Feskanich et al., "Vitamin K Intake and Hip Fractures in Women: A Prospective Study" Am J Clin Nutr., 1999; 69 (1): 74-79.

(Continued)

*Primary Examiner* — Amy L Clark
(74) *Attorney, Agent, or Firm* — Abel Law Group, LLP

(57) ABSTRACT

A micronutrient dosage unit which comprises two or more micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium in one or more specified ratios. This Abstract is not intended to define the invention disclosed in the specification, nor intended to limit the scope of the invention in any way.

44 Claims, No Drawings

OTHER PUBLICATIONS

Ubbink et al., "Vitamin Requirements for the Treatment of Hyperhomocysteinemia in Humans" J Nutr., 1994; 124 (10): 1927-1933. (Abstract).

Russell, "Vitamin Requirements of Elderly People: An Update" Am J Clin Nutr., 1993; 58 (1): 4-14 (Abstract).

Udall et al., "Vitamin Update " Pediatr Rev, 1992; 13: 185-94 (Abstract).

Schurgers et al., "Role of Vitamin K and Vitamin K-Dependent Proteins in Vascular Calcification " Z Kardiol, 2001; 90 Suppl 3:57-63 (Abstract).

"Study Demonstrates Essential role of Zeaxanthin in Eye Health," document regarding: Krinsky et al., "Biologic Mechanisms of the Protective Role of Lutein and Zeaxanthin in the Eye", Annu Rev. Nutr., 2003; 23: 171-201 (5 pages).

Zeitz et al., "Impaired Insulin Secretory Capacity in Mice Lacking a Functional Vitamin D Receptor" FASEB J, 2003; 17 (3): 509-511 (Abstract).

Shankar et al., "Zinc and Immune Function: The Biological Basis of Altered Resistance to Infection" American Journal of Clinical Nutrition; 1998, vol. 68: pp. 447S-463S (Abstract).

Newsome et al., "Oral Zinc in Macular Degeneration" Arch Ophthalmol, 1988; 106 (2): 192-198 (Abstract).

Baum et al., "Zinc Status in Human Immunodeficiency Virus Infection" J Nutr., 2000; 130 (5S Suppl): 1421S-1423S.

MacLaughlin et al., "Aging Decreases the Capacity of Human Skin to Produce Vitamin D3" J Clin Invest, 1985; 76: 1536-38 (Abstract).

Szulc et al., "Serum Undercarboxylated Osteocalcin is a Marker of the Risk of Hip Fracture in Elderly Women" J Clin Invest, 1993; 91 (4): 1769-1774. (Abstract).

Hinds et al., "Carotenoids and Retinoids: A Review of Research, Clinical, and Public Health Applications" J Clin Pharmacol, 1997; 37: 551-8 (Abstract).

Pearce et al., "The Calcium-Sensing Receptor: Insights into Extracellular Calcium Homeostasis in Health and Disease", J Endocrinol., 1997; 154 (3): 371-378 (Abstract).

Baum et al., "Selenium and Interleukins in Persons Infected with Human Immunodeficiency Virus Type I" J Infect Dis., 2000; 182 Suppl 1:S69-73 (Abstract).

Kobla et al., "Chromium, Exercise, and Body Composition" Crit Rev Food Sci Nutr., 2000; 40 (4): 291-308 (Abstract).

Hypponen et al., "Intake of Vitamin D and Risk of Type 1 Diabetes: A Birth-Cohort Study" Lancet, 2001; 358 (9292): 1500-1503 (Abstract).

Song et al., "Magnesium Intake and Plasma Concentratios of Markers of Systemic Inflammation and Endothelial Dysfunction in Women" Am J Clin Nutr., 2007; 85 (4): 1068-1074.

Freeland-Graves et al., "Models to Study Manganese Deficiency" (Chapter 3) In: Klimis-Tavatzis DL, ed. Manganese in Health and Disease. Boca Raton: CRC Press, Inc, 1994: pp. 59-86.

Melhus et al., "Excessive Dietary Intake of Vitamin A is Associated with Reduced Bone Mineral Density and Increased risk of (for) Hip Fracture" Ann Intern Med, 1998; 129: 770-8 (Abstract).

Lukaski, "Chromium as a Supplement" Annu Rev Nutr., 1999; 19: 279-302 (Abstract).

Refsum et al., "Homocysteine and Cardiovascular Disease" Annu Rev. Med, 1998; 49:31- 62 (Abstract).

Suttie, "The Importance of Menaquinones in Human Nutrition" Annu Rev Nutr., 1995; 15: 399- 417 (Abstract).

Soprano et al., "Retinoids as Teratogens" Annu Rev Nutr, 1995; 15: 111-32 (Abstract).

Knekt et al., "Antioxidant Vitamins and Coronary Heart Disease Risk " Am J Clin Nutr., 2004; 80 (6): 1508-1520.

Tosiello, "Hypomagnesemia and Diabetes Mellitus. A Review of Clinical Implications" Arch Intern Med., 1996; 156 (11): 1143-1148 (Abstract).

Wald et al., "Randomized Trial of Folic Acid Supplementation and Serum Homocysteine Levels" Arch Intern Med, 2001; 161: 695-700 (Abstract).

Luchsinger et al., "Relation of Higher Folate Intake to Lower Risk of Alzheimer Disease in the Elderly" Arch Neurol, 2007; 64 (1): 86-92 (Abstract).

"A randomized, Placebo-Controlled, Clinical Trial of High-Dose Supplementation with Vitamins C and E, Beta Carotene, and Zinc for Age-Related Macular Degeneration and Vision Loss: ADRES Report No. 8" Arch Ophthalmol, 2001; 119 (10): 1417-1436 (Abstract).

Jie et al., "Vitamin K Intake and Osteocalcin Levels in Women with and without Aortic Atherosclerosis: A Population-Based Study" Atherosclerosis, 116 (1): 117-123 (Abstract).

Simon et al., "Erythrocyte, but not Plasma, Vitamin E Concentration is Associated with Carotid Intima-Media Thickening in Asymptomatic Men at Risk for Cardiovascular Disease" Atherosclerosis, 2001; 159 (1): 193-200 (Abstract).

Selhub et al., "B Vitamins, Homocysteine, and Neurocognitive function in the Elderly" Am J Clin Nutr., 2000; 71 (2): 614S-620S.

Olson, "Benefits and Liabilities of Vitamin A and Carotenoids" J Nutr, 1996; 126: 1208S-12S (Abstract).

Pavia et al., "Beta-Carotene and Other Carotenoids as Antioxidants" J Am Coll Nutr, 1999; 18: 426-33.

Shane, "Folic Acid, Vitamin B12, and Vitamin B6" (Chapter 21) In: Stipanuk M, ed. Biochemical and Physiological Aspects of Human Nutrition, W.B. Saunders Co., 2000; pp. 483-518.

Sheng, "Sodium, Chloride, and Potassium" (Chapter 30) In: Stipanuk M, ed. Biochemical and Physiological Aspects of Human Nutrition, W.B. Saunders Company, 2000; pp. 686-710.

Kushi et al., "Dietary Antioxidant Vitamins and Death from Coronary Heart Disease in Postmenopausal Women" N Engl J Med., 1996; 334 (18): 1156-1162.

Booth et al., "Dietary Intake and Adequacy of Vitamin K" J Nutr., 1998; 128 (5): 785-788.

Tucker et al., "Potassium, Magnesium, and Fruit and Vegetable Intakes are Associated with Greater Bone Mineral Density in Elderly Men and Women" Am J Clin Nutr, 1999; 69 (4): 727-736.

Traber, "Does Vitamin E Decrease Heart Attack Risk? Summary and Implications with Respect to Dietary Recommendations" J Nutr., 2001; 131 (2): 395S-397S.

Folate, Dietary Reference Intakes for Thiamin, Riboflavin, Niacin, Vitamin B6, Folate, Vitamin B12, Pantothenic Acid, Biotin, and Choline, National Academy of Sciences,1998: 196-305.

Vitamin B12, Reference Intakes for Thiamin, Riboflavin, Niacin, Vitamin B6, Folate, Vitamin B12, Pantothenic Acid, Biotin, and Choline, National Academy of Sciences, 1998: 306-356.

Ho et al. "Practitioners' Guide to Meeting the Vitamin B-12 Recommended Dietary Allowance for People Aged 51 Years and Older" J Am Diet Assoc, 1999; 99 (6): 725-727 (Abstract).

Holben et al., "The Diverse Role of Selenium Within Selenoproteins: A Review." J Am Diet Assoc., 1999; 99 (7): 836-843 (Abstract).

Johansson et al., "Vitamin A Antagonizes Calcium Response to Vitamin D in Man" J Bone Miner Res., 2001; 16 (10): 1899-1905 (Abstract).

Promislow et al., "Retinol Intake and Bone Mineral Density in the Elderly: the Rancho Bernardo Study", J Bone Miner Res, 2002; 17 (8): 1349-1358.

Bischoff et al., "Effects of Vitamin D and Calcium Supplementation on Falls: A Randomized Controlled Trial", J Bone Miner Res., 2003; 18 (2): 343-351 (Abstract).

Gerdhem et al., "Associations Between Homocysteine, Bone Turnover, BMD, Mortality, and Fracture Risk in Elderly Women", J Bone Miner Res., Jan. 2007; 22 (1): 127-34 (Abstract).

Ballew et al., "High Serum Retinyl Esters are not Associated with Reduced Bone Mineral Density in the Third National Health and Nutrition Examination Survey, 1988-1994", J Bone Miner Res, 2001; 16: 2306-12 (Abstract).

Geusens et al., "1997 Quadriceps and Grip Strength are related to Vitamin D Receptor Genotype in Elderly Nonobese Women", J Bone Miner Res, 1997 (Abstract).

Kinsman et al., "Studies in Copper Status and Atherosclerosis", Biochem Soc Trans., 1990; 18 (6): 1186-1188 (Abstract).

Maier et al., "Low Magnesium Promotes Endothelial Cell Dysfunction: Implications for Athorsclerosis, Inflammation and Thrombosis", Biochim Biophys Acta., 2004; 1689 (1): 13-21 (Abstract).

Lin et al., "The Pleiotropic Actions of Vitamin D. ", Bioessays, 2004; 26 (1): 21-28 (Abstract).

Roy et al., "Supplementation with Selenium and Human Immune Cell Functions. I. Effect on Lymphocyte Proliferation and Interleukin 2 Receptor Expression", Biol Trace Elem Res., 1994; 41 (1-2): 103-114 (Abstract).

Kiremidjian-Schumacher et al., "Selenium and Immunocompetence in Patients with Head and Neck Cancer", Biol Trace Elem Res., 2000; 73 (2): 97-111 (Abstract).

Rohde et al., "Bone Resorption Activity of All-Trans Retinoic Acid is Independent of Vitamin D in Rats.", J Nutr., 2003; 133 (3): 777-783.

Zittermann, "Vitamin D in Preventive Medicine: Are we Ignoring the Evidence", Br J Nutr., 2003; 89 (5): 552-572 (Abstract).

Remer et al., "Increased Risk of Iodine Deficiency with Vegetarian Nutrition ", Br J Nutr., 1999; 81 (1): 45-49 (Abstract).

Bunk et al., "Dietary Zinc Deficiency Decreases Plasma Concentrations of Vitamine E", Proc Soc Exp Biol Med, 1989; 190: 379-84 (Abstract).

Birkett, "Comments on a Meta-Analysis of the Relation Between Dietary Calcium Intake and Blood Pressure", Am J Epidemiol, 1998; 148 (3): 223-228; discussion 232-223 (Abstract).

Davies et al., "Calcium Intake and Body Weight", J Clin Endocrinol Metabol., 2000; 85 (12): 4635-4638 (Abstract).

Li, "1,25-Dihydroxyvitamin D(3) is a Negative Endocrine Regulator of the Renin-Angiotensin System", J Clin Invest., 2002; 110 (2): 229-238.

Sigmund, "Regulation of Renin Expression and Blood Pressure by Vitamin D(3)", J Clin Invest., 2002; 110 (2): 155-156.

Boaz et al., "Secondary Prevention with Antioxidants of Cardiovascular Disease in Endstage Renal Disease (SPACE): Randomised Placebo-Controlled Trial", Lancet, 2000; 356 (9237): 1213-1218 (Abstract).

Forsyth et al., "Osteotoxicity After Chronic Dietary Administratio of 13-Cis-Retinoic Acid, Retinyl Palmitate or Selenium in Mice Exposed to Tumor Initiation and Promotion ", Life Sci, 1989; 45: 2149-56 (Abstract).

Maebashi et al., "Therapeutic Evaluation of the Effect of Biotin on Hyperglycemia in Patients with Non-Insulin Dependent Diabetes Mellitus", J. Clin. Biochem. Nutr., 14, 211-218, 1993.

Higdon, "Biotin", Linus Pauling Institute, updated Jun. 1, 2004 (10 pages).

Higdon, "Calcium", Linus Pauling Institute, updated Jnue 2007 (24 pages).

Althuis et al., "Glucose and Insulin Responses to Dietary Chromium Supplements: A Meta-Analysis", Am J Clin Nutr., 2002; 76 (1): 148-155.

Calcium Fact Sheet, Northwestern University, updated Sep. 21, 2006 (5 pages).

Stendig-Lindberg et al., "Trabecular Bone Density in a Two Year Controlled Trial of Peroral Magnesium in Osteoporosis", Magnes Res., 1993 (Abstract).

Kies, "Bioavailability of Manganese. In: Klimis-Tavatzis DL, ed. Manganese in Health and Disease. Boca Raton", CRC Press, Inc, 1994, pp. 40-58.

Shetlar et al., "The Role of Manganese in Wound Healing In: Klimis-Tavatzis DL, ed. Manganese in Health and Disease. Boca Raton (Chapter 9)", CRC Press, Inc, 1994, pp. 145-157.

Friedman et al., "Manganese Balance and Clinical Observations in Young Men Fed a Manganese-Deficient Diet", J Nutr., 1987 (Abstract).

"Vitamin B12 Natural Standards Patient Monograph [www.mayoclinic.com/health/vitamin-B12/NS_patient-Vitaminb12]", Mayo Clinic, Dec. 1, 2010 (7 pages).

Davies et al., "Age-Related Decreases in Chromium Levels in 51,665 Hair, Sweat, and Serum Samples from 40,872 Patients—Implications for the Prevention of Cardiovascular Disease and Type II Diabetes Mellitus", Metabolism, 1997 (Abstract).

Farrell et al., "Vitamin E In: Shils M, Olson JA, and Shike M, ed. Modern Nutrition in Health and Disease, 8th ed., Philadelphia, PA (Chapter 18)", Lea and Gebiger, 1994, pp. 326-341.

Rude et al., "Magnesium. In: Shils ME, Shike M, Ross AC, Caballero B, Cousins RJ, eds. Modern Nutrition in Health and Disease. 10th ed Baltimore", Lippincott Williams & Wilkins, 2006, pp. 223-247.

Traber, "Vitamin E1. In Shils ME, Olson JA, Shike M, Ross AC. ed Modern Nutrition in Health and Disease, 10th ed Baltimore", Williams & Wilkins, 1999, pp. 396-411.

Weaver et al., "Calcium. In: Shils M, Olson JA, Shike M, Ross AC, eds. Modern Nutrition in Health Disease. 9th ed. Baltimore", Williams & Wilkins, 1999, pp. 141-155.

Weir et al., "Vitamin B12 "Cobalamin". InL: Shils M, ed. Modern Nutrition in Health and Disease. 9th ed. Baltimore", Williams & Wilkins, 1999, pp. 447-458.

Shils, "Magnesium. In: Shills M, Olson JA, Shike M, Ross AC, eds. Modern Nutrition in Health and Disease. 9th ed. Baltimore", Williams & Wilkins, 1999, pp. 169-192.

Turnlund, "Copper1. In: Shils ME, Olson JA, Shike M, Ross AC, Caballero B, Cousins RA, eds.Modern Nutrition in Health and Disease. 10th ed. Baltimore", Williams & Wilkins, 2006, pp. 286-299.

Hetzel et al., "Iodine. In: Shils M., Olson JA, Shike M, Ross AC, eds. Modern Nutrition in Health and Disease. 9th ed. Baltimore", Williams & Wilkins, 1999, pp. 253-264.

McCormick, "Riboflavin: In Shils M, Olson JA, Shike M, Ross AC, eds. Modern Nutrition in Health Disease. 9th ed. Baltimore", Williams & Wilkins, 1999, pp. 391-399.

Burk et al., "Selenium. In: Shils M, Olson JA, Shike M, Ross AC, eds. Modern Nutrition in Health Disease. 9th ed. Baltimore", Williams & Wilkins, 1999, pp. 265-276.

Nielsen, "Ultratrace Minerals1. In: Shils ME, Olson JA, Shike M, Ross AC, eds. Modern Nutrition in Health and Disease. 9th ed. Baltimore", Williams & Wilkins, 1999, pp. 283-303.

Ross, "Vitamin A and Retinoids. In: Shils ME, Olson JA, Shike M, Ross AC, eds. Modern Nutrition in Health and Disease. 9th ed. Baltimore", Lippincott Williams & Wilkins, 1999, pp. 305-327.

Leklem, "Vitamin B6. In: Shils ME, Olson JA, Shike M, Ross AC, eds. Modern Nutrition in Health and Disease. 9th ed. Baltimore", Williams & Wilkins, 1999, pp. 413-421.

Olson, "Vitamin K. In: Shils ME, Olson JA, Shike M, Ross AC, eds. Modern Nutrition in Health and Disease. 9th ed. Baltimore", Williams & Wilkins, 1999, pp. 363-380.

King et al., "Zinc. In: Shils ME, Olson JA, Shike M, Ross AC, eds. Modern Nutrition in Health and Disease. 9th ed. Baltimore", Williams & Wilkins, 1999, pp. 223-239.

Lindenbaum et al., "Neuropsychiatric Disorders Caused by Cobalamin Deficiency in the Absence of Anemia or Macrocytosis", N Engl J Med, 1988 (Abstract).

Wang et al., "Vitamin B(12) and Folate in Relation to the Development of Alzheimer's Disease", Neurology, 2001 (Abstract).

Clarke et al., "Vitamin B12 and Serum Total Homocysteine Levels in Confirmed Alzheimer Disease", Arch Neurol., 1998; 55: 1449-55.

Masaki et al., "Association of Vitamin E and C Supplement Use with Cognitive Function and Dementia in Elderly Men", Neurology, 2000 (Abstract).

Quinlivan et al., "Importance of Both Folic Acid and Vitamin B12 in Reduction of Risk of Vascular Disease", Lancet, 2002 (Abstract).

Munger et al., "Vitamin D Intake and Incidence of Multiple Sclerosis", Nueurology, 2004 (Abstract).

Reaven, "Insulin Resistance Syndrome Key to Diseases", NewsMax.com wires, Aug. 3, 2007 (1 page).

Harbige, "Nutrition and Immunity with Emphasis on Infection and Autoimmune Disease", Nutr Health, 1996 (Abstract).

Futoryan et al., "Retinoids and the Skin", Nutr Rev, 1994 (Abstract).

Sojka et al., "Magnesium Supplementation and Osteoporosis ", Nutr Rev, 1995 (Abstract).

Booth, "Skeletal Functions of Vitamin K-Dependent Proteins: Not Just for Clotting Anymore", Nutr Rev, 1997 (Abstract).

Stoecker et al., "Effects of Chromium on Body Composition and Weight Loss", Williams & Wilkins, 1999 (Abstract).

Shearer, "The Roles of Vitamin D and K in Bone Health and Osteoporosis Prevention", Proc Nutr Soc., 1997 (21 pages).

Blumberg, "Nutritional Needs of Seniors", Journal of the American College of Nutrition, vol. 16, Issue 6, 1997 (Abstract).

Gale et al., "Plasma Antioxidant Vitamins and Carotenoids and Age-Related Cataract", Ophthalmology, 2001 (Abstract).

Cumming et al., "Diet and Cataract: The Blue Mountains Eye Study", Ophthalmology, 2000 (Abstract).

Shechter et al., "Oral Magnesium Theraphy Improves Endothelial Function in Patients with Coronary Artery Disease", Circulation, 2000, pp. 1-12.
"Osteoporosis Prevention, Diagnosis, and Therapy", NIH Consensus Statement Online, Mar. 2000, pp. 1-27.
Peacock et al., "Relationship of Serum and Dietary Magnesium to Incident Hypertension: The Atherosclerosis Risk in Communities (ARIC) Study", ANN Epidemiol, 1999 (Abstract).
Combs et al., "Chemopreventive Agents: Selenium", Pharmacol Ther., 1998 (Abstract).
Herbert, "(Chapter 20) Vitamin B-12. In: Ziegler EE, Filer LJ, eds. Present Knowledge in Nutrition. 7th ed. Washington D.C.", ILSI Press, 1996, pp. 191-205.
Keen et al., "(Chapter 33) Manganese. In: Ziegler EE, Filer LJ, eds. Present Knowledge in Nutrition. 7th ed. Washington D.C.", ILSI Press, 1996, pp. 334-343.
Hayes et al., "The Immunological Functions of the Vitamin D Endocrine System", Cell Mol Biol., 2003 (Abstract).
Mertz, "Chromium in Human Nutrition: a Review", J Nutr., 1993, (Abstract).
Gokce et al., "Long-Term Ascorbic Acid Administration Reverses Endothelial Vasomotor Dysfunction in Patients with Coronary Artery Disease", Circulation, 1999 (Abstract).
Doshi et al., "Folic Acid Improves Endothelial Function in Coronary Artery Disease Via Mechanisms Largely Independent of Homocysteine Lowering", Circulation, 2002, pp. 1-6.
Malinow, "Plasma Homocyst(e)ine and Arterial Occlusive Disease: A mini-Review", Clin Chem, 1995 (Abstract).
Shils et al., "(Chapter 25) Magnesium. In: Ziegler EE, Filer LJ, eds. Present Knowledge in Nutrition. 7th ed. Washington D.C.", ILSI Press, 1996, pp. 256-264.
Suttie et al., "(Chapter 14) Vitamin K. In: Ziegler EE, Filter LJ, eds. Present Knowledge in Nutrition. 7th ed. Washignton D.C.", ILSI Press, 1996, pp. 137-145.
Seshadri et al., "Plasma Homocysteine as a Risk Factor for Dementia and Alzheimer's Disease", N Engl J Med., 2002, pp. 1-14.
Vollset et al., "Plasma total Homocysteine and Cardiovascular Mortality: The hordoland Homocysteine Study 1,2,3", Am J Clin Nutr., Jul. 2001, pp. 1-12.
Anderson et al., "Potential Antioxidant Effects of Zinc and Chromium Supplementation in People with Type 2 Diabetes Mellitus", J Am Coll Nutr., 2001 (Abstract).
Plotnikoff et al., "Prevalence of Severe Hypovitaminosis D in Patients with Persistent, Nonspecific Musculoskeletal and inordinate Fatigue", Mayo Clin Proc., 2003 (Abstract).
Ross, "Vitamin A and Public Health: Challenges for the Next Decade", Proc Nutr Soc; 1998 (Abstract).
Thurnham et al., "Optimal Nutrition: Vitamin A and the Carotenoids", Proc Nutr Soc., 1999 (Abstract).
Olson et al., "Antioxidants in Health and Disease: Overview ", Proc Soc Exp Biol Med, 1992 (Abstract).
Brown et al., "A Prospective Study of Carotenoid Intake and Risk of Cataract Extraction in US Men", Am J Clin Nutr., 1999, pp. 1-14.
Robins, "Psychiatric Disorders in America, The Epidemiologic Catchment Area Study", The Free Press, 1990, pp. 1-6.
Talbott et al., "Pyridoxine Supplementation: Effect on Lymphocyte Responses in Elderly Persons", Am J Clin Nutr., 1987 (Abstract).
Dawson-Hughes et al., "Rates of Bone Loss in Postmenopausal Women Randomly Assigned to one of two Dosages of Vitamin D", Am J Clin Nutr., 1995, (Abstract).
Witteman et al., "Reduction of Blood Pressure with Oral Magnesium Supplementation in Women with Mild to Moderate Hypertension", Am J Clin Nutr., 1994 (Abstract).
Zemel et al., "Regulation of Adiposity by Dietary Calcium", FASEB J, 2000, pp. 1-13.
Riggs et al., "Relations of Vitamin B-12, Vitamin B-6, Folate, and Homocysteine to Cognitive Performance in the normative Aging Study", Am J Clin Nutr., 1996, (Abstract).
Jacques et al., "The Relationship Between Riboflavin and Plasma Total Homocysteine in the Framingham Offspring Cohort is Influenced by Folate Status and the C677T Transition in the Methylenetetrahydrofolate Reductose Gene", J Nutr., 2002, pp. 1-10.
McCormick, "Two Interconnected B Vitamins: Riboflavin and Pyridoxine", The American Physiological Society, 1989, p. 1170.
Lowik et al., "Interrelationships Between Riboflavin and Vitamin B6 Among Elderly People (Dutch Nutrition Surveillance System)", Int J Vitam Nutr Res., 1994, pp. 1.
Madigan et al., "Riboflavin and Vitamin B-6 intakes and Status and Biochemical Response to Riboflavin Supplementation in Free-Living Elderly People", Am J Clin Nutr., 1998, pp. 1.
Jeejeebhoy, "The Role of Chromium in Nutrition and Therapeutics and as a Potential Toxin", Nutr-Rev., 1999, pp. 1.
Quinlivan et al., "Importance of Both Folic Acid and Vitamin B12 in Reduction of Risk of Vascular Disease", Lancet, 2002, pp. 1.
Salonen et al., "Association Between Cardiovascular Death and Myocardial Infarction and Serum Selenium in a Matched-Pair Longitudinal Study", Lancet, 1982, pp. 1.
Stephens et al., "Randomised Controlled Trial of Vitamin E in Patients with Coronary Disease: Cambridge Heart Antioxidant Study (CHAOS)", Lancet, 1996, pp. 1-2.
Krause et al., "Ultraviolet B and Blood Pressure", Lancet, 1998, pp. 1.
Duffy et al., "Treatment of Hypertension with Ascorbic Acid", Lancet, 1999, pp. 1.
Duffield-Lillico et al., "Selenium Supplementation, Baseline Plasma Selenium Status and Incidence of Prostate Cancer: An Analysis of the Complete Treatment Period of the Nutritional Prevention of Cancer Trial", BJU Int, May 2003, pp. 608-612.
Simon et al., "Serum Ascorbic Acid and Other Correlates of Self-Reported Cataract Among Older Americans", J Clin Epidemiol, 1999, pp. 1.
Snowdon et al., "Serum Folate and the Severity of Atrophy of the Neocortex in Alzheimer Disease: Findings from the Nun Study", Am J Clin Nutr., 2000, pp. 1-12.
Michaelsson et al., "Serum Retinol Levels and the Risk of Fracture", N Engl J Med., 2003, pp. 1-12.
Blostein-Fujii et al., "Short-Term Zinc Supplementation in Women with Non-Insulin-Dependent Diabetes Mellitus: Effects on Plasma 5'-Nucleotidase Activities, Insulin-Like Growth Factor I Concentration, and Lipoprotein Oxidation Rates in Vitro", Am J Clin Nutr., 1997, pp. 1.
Deluca et al., "Vitamin D: Its Role and Uses in Immunology", FASEB J, 2001, pp. 1-14.
Gerster et al., "Vitamin A-Functions, Dietary Requirements and Safety in Humans", Int J Vitam Nutr Res, 1997, pp. 1.
Feskanich et al., "Vitamin A Intake and Hip Fractures Amond Postmenopausal Women", JAMA, 2002, pp. 1-14.
Vanuzzo et al., "Both Vtiamin B6 and Total Homocysteine Plasma Levels Predict Long-Term Atherothrombotic Events in Healthy Subject", Eur Heart J., 2007, pp. 1-20.
Meydani et al., "Vitamin B-6 Deficiency Impairs Interleukin 2 Production and Lymphocyte Proliferation in elderly Adults", Am J Clin Nutr., 1991, pp. 1.
Ribaya-Mercado et al.. "Vitamin B-6 Requirements of Elderly Men and Women", J Nutr., 1991, pp. 1.
Stabler et al., "Vitamin B-12 Deficiency in the Elderly: Current Dilemmas", Am J Clin Nutr., 1997, pp. 1.
Holick et al., "Vitamin D: Importance in the Prevention of Cancers, Type I Diabetes, Heart Disease, and Osteoporosis", Am J Clin Nutr., 2004, pp. 1-21.
Hellerstein, "Is Chromium Supplementation Effective in Managing Type II Diabetes?", Nutr Rev, 1998, pp. 1.
Whiting et al., "Excess Retinol Intake May Explain the High Incidence of Osteoporosis in Northern Europe" Nutr Rev 1999;57:249-50 (Abstract).
Anderson, "Effects of Chromium on Body Composition and Weight Loss", Nutr Rev, 1998, pp. 1.
Jacques et al., "Long-Term Nutrient Intake and 5-Year Change in Nuclear Lens Opacities", Arch Ophthalmol, 2005, pp. 1-18.
Hankinson et al., "Nutrient Intake and Cataract Extraction in Women: A prospective Study", BMJ, 1992, pp. 1.
Ursini et al., "Dual Function of the Selenoprotein PHGPs During Sperm Maturation", Science, 1999, pp. 1.
Strause et al., "Spinal Bone Loss in Postmenopausal Women Supplemented with Calcium and Trace Minerals", J Nutr., 1994, pp. 1.

Suadicani, "Serum Selenium Concentration and Risk of Ischaemic Heart Disease in a Prospective Cohort Study of 3000 Males", Atherosclerosis, 1992, pp. 1.

Nielsen et al., "Effect of Dietary Boron on Mineral, Estrogen and Testosterone Metabolism in Postmenopausal Women. Journal of the Federation of American Societies for Experimental Biology ", The FASEBJ Journal, vol. 1, 1987, pp. 1.

Beck et al., "Glutathione Peroxidase Protects Mice from Viral-Induced Myocarditis", Faseb J, 1998, pp. 1-13.

Ross et al., "Vitamin A and Retinoids in Antiviral Responses", FASEB Journal, vol. 10 , 1996, pp. 1.

Leske et al., "Antioxidant Vitamins and Nuclear Opacities: The Longitudinal Study of Cataract", Ophthalmology, 1998, pp. 1.

Carr et al., "Toward a New Recommended Dietary Allowance for Vitamin C Based on Antioxidant and Health Effects in Humans", Am J Clin Nutr., 1999, pp. 1-44.

Penland et al., "The Inprotance of Boron Nutrition for Brain and Psychological Function", Environ Health Perspect, 1994, pp. 1.

Thomson et al., "Urinary Iodine and Thyroid Status of New Zealand Residents", Kluwer Academic Press, 2000, pp. 1-2.

Pfeifer et al., "Effects of a Short-Term Vitamin D(3) and Calcium Supplementation on Blood Pressure and Parathyroid Hormone Levels in Elderly Women", J Clin Endocrinol Metab., 2001, pp. 1.

Sutton et al., "Vitamin D: More Than a "Bone-A-Fide" Hormone", Mol Endocrinol, 2003, pp. 1.

Stampfer et al., "Vitamin E Consumption and the Risk of Coronary Disease in Women", N Engl J Med, 1993, pp. 1-13.

Rimm et al., "Vitamin E Consumption and the Risk of Coronary Heart Disease in Men", N Engl J Med, 1993, pp. 1-12.

Meydani et al., "Vitamin E Supplementation and in Vivo Immune Response in Healthy Elderly Subjects. A Randomized Controlled Trial", Jama, 1997, pp. 1.

Jain et al., "Effect of Modest Vitamin E Supplementation on Blood Glycated Hemoglobin and Triglyceride Levels and Red Cell Indices in Type I Diabetic Patients", J Am Coll Nutr., 1996, pp. 1.

Baik et al., "Vitamin B12 Deficiency in the Elderly", Annu Rev Nutr., 1999, pp. 1.

Griffin et al., "Vitamin D and its Analogs as Regulators of Immune Activation and Antigen Presentation", Annu Rev Nutr., 2003, pp. 1.

Lyle et al., "Antioxidant Intake and Risk of Incident Age-related Nuclear Cataracts in the Beaver Dam Eye Study", Am J Epidemiol, 1999, pp. 1.

Azen et al., "Effect of Supplementary Antioxidant Vitamin Intake on Carotid Arterial wall Intima-Media Thickness in a Controlled Clinical Trial of Cholesterol Lowering", Circulation, 1996, pp. 1-9.

Gale et al., "Antioxidant Vitamin Status and Carotid Atherosclerosis in the Elderly", Am J Clin Nutr., 2001, pp. 1-13.

Jacques et al., "Long-Term Nutrient Intake and Early Age-Related Nuclear Lens Opacities", Ophthalmol, 2001, pp. 1-2.

Leske et al., "Biochemical Factors in the Lens Opacities. Case-Control Study. The Lens Opacities Case-Control Study Group", Arch Ophthalmol, 1995, pp. 11.

Doshi et al., "Folate Improves Endothelial Function in Coronary Artery Disease", Arterioscler Thromb Vasc Biol, 2001, pp. 1-15.

Merlino et al., "Vitamin D Intake is Inversely Associated with Rheumatoid Arthritis: Results from the Iowa Women's Health Study", Arthritis Rheum, 2004, pp. 1.

Selhub et al., "Association Between Plasma Homocysteine Concentrations and Extracranial Carotid-Artery Stenosis", N Engl J Med, 1995, pp. 1-12.

Salgueiro et al., "Zinc Status and Immune System Relationship: A Review.", Biol Trace Elem Res., 2000, pp. 1.

Coggeshall et al., "Biotin Status and Plasma Glucose Levels in Diatetics", Ann NY Acad Sci., 1985, pp. 1.

Furie et al., "Vitamin K-Dependent Biosynthesis of Gamma-Carboxyglutamic Acid", Blood, 1999, pp. 1-20.

"Homocysteine Lowering Trialists' Collaboration. Lowering Blood Homocysteine with Folic Acid based Supplements: Meta-Analysis of Randomised Trials. Homocysteine Lowering Trialsits' Collaboration", BMJ, 1998, pp. 1.

Arunabh et al., "Body Fat Content and 25-Hydroxyvitamin D Levels in Healthy Women", J Clin Endocrinol Metab., 2003, pp. 1-11.

Dawson-Hughes et al., "Effect of Withdrawal of Calcium and Vitamin D Supplements on Bone Mass in Elderly Men and Women", Am J Clin Nutr., 2000, pp. 745-750.

Feskanich et al., "Calcium, Vitamin D, Milk Consumption, and Hip Fractures: A Prospective Study Among Postmenopausal Women", Am J Clin Nutr., 2003, pp. 1-16.

Jialal et al., "Effect of Vitamin E, Vitamin C and Beta-Carotene on LDL Oxidation and Atherosclerosis", Can J Cardiol, 1995, pp. 1.

Lonn et al., "Is There a Role for Antioxidant Vitamins in the Prevention of Cardiovascular Diseases? An update on Epidemiological and Clinical Trials Data", Can J Cardiol, 1997, pp. 1.

Klevay, "Cardiovascular Disease from Copper Deficiency—a History ", J Nutr., 2000, pp. 1.

Williams et al., "S-Adenosylmethionine (SAMe) as Treatment for Depression: A Systematic Review", Clin Invest Med, 2005, pp. 1.

Hutto et al., "Folate and Cobalamin in Psychiatric Illness", Compr Psychiatry, 1997, pp. 1.

Sano et al., "A Controlled Trial of Selegiline, Alpha-Tocopherol, or Both as Treatment for Alzheimer's Disease. The Alzheimer's Disease Coorperative Study", N Engl J Med., 1997, pp. 1-12.

Percival, "Copper and Immunity", Am J Clin Nutr., 1998, pp. 1.

Conlan et al., "Serum Copper Levels in Elderly Patients with Femoral-Neck Fractures", Age Ageing, 1990, pp. 1.

Eaton-Evans et al., "Copper Supplementation and the Maintenance of Bone Mineral Density in Middle-Aged Women ", J Trace Elem Exp Med, 1996, pp. 1.

Levander, "Coxsackievirus as a Model of Viral Evolution Driven by Dietary Oxidative Stress", Nutr Rev., 2000, pp. 1.

Gerhard et al., "Homocysteine and Atherosclerosis", Curr Opin Lipidol., 1999, pp. 1.

Paolisso et al., "Daily Magnesium Supplements Improve Glucose Handling in Elderly Subjects", Am J Clin Nutr., 1992, pp. 1.

Lin et al., "Dairy Calcium is Related to Changes in Body Composition During a Two-Year Exercise Intervention in young Women", J Am Coll Nutr., 2000, pp. 1.

Levander et al., "Deliberations and Evaluations of the Approaches, Endpoints and Paradigms for Selenium and Iodine Dietary Recommendations ", J Nutr., 1996, pp. 1.

Jacques et al., "Determinants of Plasma Total Homocysteine Concentration in the Framingham Offspring Cohort", Am J Clin Nutr., 2001, pp. 1-13.

Nath et al., "Superoxide Dismutase in Diabetic Polymorphonuclear Leukocytes", Diabetes, 1984, pp. 1.

El-Yazigi et al., "Urinary Excretion of Chromium, Copper, and Manganese in Diabetes Mellitus and Associated Disorders", Diabetes, 1991, pp. 1.

Holick, "Vitamin D: A Millenium Perspective", J Cell Biochem., 2003, pp. 1.

Ooms et al., "Prevention of Bone Loss by Vitamin D Supplementation in Elderly Women: A Randomized Double-Blind Trial", Journal of Clincal Endocrinology & Metabolism, vol. 80 1995, pp. 1.

Harris et al., "Vitamin D Insufficiency and Hyperparathyroidism in a Low Income, Multiracial, Elderly Population", J Clin Endocrinol Metab., 2000, pp. 1.

Vergnaud et al., "Undercarboxylated Osteocalcin Measured with a Specific Immunoassay Predicts Hip Fracture in Elderly Women: The EPILOS Study", J Clin Endocrinol Metab, 1997, pp. 1.

Hollowell et al., "Iodine Nutrition in the United States. Trends and Public health implications: Iodine Excretion Data from national Health and Nutrition Examination Surveys I and III (1971-1974 and 1988-1994)", J Clin Endocrinol Metab., 1998, pp. 1-2.

Lopez-Sobaler et al., "The Influence of Vitamin B2 Intake on the Activation Coefficient of Erythrocyte Glutation Reductase in the Elderly", J Nutr Health Aging, 2002, pp. 1.

Zhang et al., "Biotin Administration Improves the Impaired Glucose Tolerance of Streptozotocin-Induced Diabetsin Wistar Rats", J Nutr Sci Vitaminol, 1997, pp. 1.

Bhutta et al., "Prevention of Diarrhea and Pneumonia by Zinc Supplementation in Children in Developing Countries: Pooled Analysis of Randomized Controlled Trials" Zinc Investigator's Collaborative Group. J. Pediatr. 1999; 135(6):689-697 (Abstract).

Stanger et al., "Effects of Folate Treatment and homocysteine Lowering on Resistance Vessel Reactivity in Atherosclerotic Subjects", J Pharmacol Exp Ther , 2002, pp. 1-12.
Abraham et al., "A Total Dietary Program Emphasizing Magnesium Instead of Calcium. Effect on the Mineral Density of Calcaneous Bone in postmenopausal Women on hormonal Therapy", J Reprod Med., 1990, pp. 1-7.
Eaton-Evans et al., "Copper Supplementation and the Mainenance of Bone Mineral Density in Middle-Aged Women", J Trace Elem Exp Med, 1996, pp. 1.
Mielcarz et al., "Leucocyte Copper, a Marker of Copper Body Status is Low in Coronary Artery Disease", J Trace Elem Med Biol., 2001, pp. 1.
Knekt et al., "Antioxidant Vitamin Intake and Coronary Mortality in a Lingitudinal Population Study", Am J Epidemiol, 1994, pp. 1.
Kelley et al., "Effects of Low-Copper Diets on Human Immunie Response", Am J Clin Nutr., 1995, pp. 1.
Need et al., "Effects of Skin Thickness, Age, Body Fat, and Sunlight on Serum 25-Hydroxyvitamin D", Am J Clin Nutr., 1993, pp. 1.
Orwoll et al., "Effects of Vitamin D on Insulin and Glucagon Secretion in Non-Insulin- Dependent Diabetes Mellitus", Am J Clin Nutr., 1994, pp. 1.
Delle Chiaie et al., "Efficacy and Tolerability of Oral and Intramuscular S-adenosyl-L-methionine 1,4-butanedisulfonate (SAMe) in the Treatment of Major Depression", Am J Clin Nutr., 2002, pp. 1-12.
Lips, "Vitamin D deficiency and secondary hyperparathyriodism in the elderly", Endocrine Rev, 2001, pp. 1.
Holick, "Vitamin D", Curr Opin Endocrinal Diabetes, 2002, 9:87-89 (Abstract).
Romero-Navarro et al., "Biotin Regulation of Pancreatic Glucokinase and Insulin in Primary Cultured Rat Islets and in Biotin deficient Rats*", Endocrinology, vol. 140, No. 10, 1999, pp. 4595-4600.
Green, "Plasma Boron and the Effects of Boron Supplementation in Males", Health Perspect, 1994, 102 (Supp 7):73-77 (Abstract).
Enstrom et al., "Vitamin C Intake and Mortality Among a Sample of the United States Population", Epidemiology, 1992, 3(3):194-202 (Abstract).
Uauy et al., "Essentiality of Copper in Humans", Am J. Clin. Nutr., 1998, pp. 1.
Cherubini et al., "High Vitamin E Plasma Levels and Low Low-Density Lipoprotein Oxidation are Associated with the Absence of Atherosclerosis in Octogenarians", J Am Geriatr Soc., 2001, pp. 1.
Chapuy et al., "Effect of Calcium and Cholecalciferol Treatment for Three Years on Hip Fractures in Elderly Women", BMJ, 1994, pp. 1-4.
Wang et al., "Plasma Extracellular Superoxide Dismutase Levels in an Australian Population With Coronary Artery Disease", Arterioscler Thromb Vasc Biol, 1998, pp. 1-13.
Appel et al., "A Clinical Trial of the Effects of Dietary Patterns on Blood Pressure", N Engl J Med., 1997, pp. 1-13.
Chasan-Taber et al., "A Prospective Study of Carotenoid and VitaminA Intakes and Risk of Cataract Extraction in US Women", Am J Clin Nutr., 1999, pp. 1-13.
Boushey et al., "A quantitative Assessment of Plasma Homocysteine as a Risk Factor for Vascular Disease", JAMA, 1995, 274(13):1049-1057 (Abstract).
Perla-Kajan et al. "Mechanisms of Homocystein Toxicity in Humans" Amino Acids 2007 (Abstract).
Bressa, "S-adenosyl-1-methionine (SAMe) as antidepressant", Acta Neurol Scand Suppl., 1994, pp. 1.
Ross et al., "The Function of Vitamin A in Cellular Growth and Differentiation, and its roles During Pregnancy and Lactation", Adv. Exp Med Biol, 1994, pp. 1.
Holick et al., Age, Vitamin D, and Solar Ultraviolet >> The Lancet, Nov. 4, 1989, pp. 1104-1105.
Stoecker, "Chromium", Williams & Wilkins, 19999, pp. 277-282.
Higdon, "Iodine", Linus Pauling Institute, updated Apr. 11, 2003 (13 pages).
National Academy of Sciences et al., "Dietary Reference Intakes for Vitamin C, Vitamin E, Selenium and Carotenoids", Institute of Medicine, 2000, pp. 1-529.
National Academy of Sciences et al., "Dietary Reference Intakes for Vitamin A, Vitamin K, Arsenic, Boron, Chromium, Copper, Iodine, Iron, Manganese, Molybdenum, Nickel, Silicon, Vanadium, and Zinc", National Academy Press, 2001, pp. 1-797.
Higdon, "Magnesium", Linus Pauling Institute, updated Aug. 2007 (24 pages).
Haan et al., "B Vitamins, and the incidence of Dementia and Cognitive Impairment", Abstract, Feb. 2007, pp. 1-13.
Leach et al., "Handbook of Nutritionally Essential Mineral Elements", Manganese, 1997, pp. 335-355.
Rostand, "Ultraviolet Light May Contribute to Geographic and Racial Blood Pressure Differences", 1997, 30(2 Pt 1):150-156.
Kawano et al., "Effects of Magnesium Supplementation in Hypertensive Patients", 1998, 32(2):260-265.
Heresi et al., "Phagocytosis and Immunoglobulin Levels in Hypocupremic Children", Nutr. Res. 1985, 5:1327-1334 (Abstract).
Davi et al., "In Vivio Formation of 8-Iso-Prostaglandin ƒ2alpha and Platelet Activation in Diabetes Mellitus", 1999, 99(2):224-229.
Heaney, Mayo Clin Proc. 2006, "Nutrition and Chronic Disease" (7 pages).
Inomata et al., "Effect of 1 Alpha (OH)-Vitamin D3 on Insulin Secretion in Diabetes Mellitus", 1986, 1(3):187-192 (Abstract).
Malek et al. "Serum Copper as a Marker of Inflammation in Prediction of Short Term Outcome in High Risk Patients with Chronic Heart Failure" Int. J. Cardiol. 2006: 113(2):e51-53 (Abstract).
Borissova et al. "The Effect of Vitamin D3 on Insulin Secretion and Peripheral Insulin Sensitivity in Type 2 Diabetic Patients" Int. J. Clin. Pract. 2003:57(4):258-261 (Abstract).
Jacques et al. "The Potential Preventive Effects of Vitamins for Cataract and Age-Related macular Degeneration" Int J Vitam Nutr Res. 1999; 69(3):198-205 (Abstract).
Feskanich et al., "Vitamin A Intake and Hip Fractures Among Postmenopausal Women", JAMA 2002, 287(1):47-54.
Gale et al., "Lutein and Zeaxanthin Status and Risk of Age-Related Macular Degeneration", Investigative Ophthalmology & Visual Science, vol. 44. No. 6, Jun. 2003, pp. 2461-2465.
McQuillan et al., "Antioxidant Vitamins and the risk of Carotid Atherosclerosis", J Am Coll Cardiol., 2001, 38(7):1788-1794 (Abstract).
Osganian et al., "Vitamin C and Risk of Coronary Heart Disease in Women", J Am Coll Cardiol., 2003, 42(2):246-252 (Abstract).
De Pee et al., "Dietary Carotenoids and their role in combating vitamin A deficiency", Eur J Clin Nutr, Jul. 1996, 50 Suppl 3:S38-53 (Abstract).
Kardinaal et al., "Association Between Toenail Selenium and Risk of Acute Myocardial Infarction in European Men", Am J Epidemiol, vol. 145, No. 4, 1997, pp. 373-379.
Thomson et al., "Long Term Dietary Supplementation with Zeaxanthin Reduces Photoreceptor Death in Light-Damaged Japanese Quail", Exp Eye Res., Nov. 2002, 75(5):529-542 (Abstract).
Muszynska et al., "The Mechanism of Daunorubicin-Induced Inhibition of Prolidase Activity in hman Skin Fibroblasts and its Implication to Impaired Collagen Biosynthesis", Exp Toxicol Pathol., 2002 (Abstract).
Willett et al., "Folate and Vitamin B6 from Diet and Supplements in Relation to Risk of Coronary Heart Disease Among Women", Journal of the American Medical Assoc., 1998, 279(5):359-364.
Higdon et al., "Vitamin A", Linus Pauling Institute, updated Dec. 12, 2003 (16 pages).
Higdon et al., "Vitamin C", Linus Pauling Institute, updated Jan. 31, 2006 (17 pages).
Ebly et al., "Folate Status, Vascular Disease and Cognition in Elderly Canadians", Age Ageing, 1998, 27(4):485-491 (Abstract).
Nourhashemi et al., "Alzheimer Disease: Protective Factos 1, 2", Am J Clin Nutr., 2000, 71(2):643S-649S.
Liao et al., "Is Low Magnesium Concentration a Risk Factor for Coronary Heart Disease?", Am Heart J. , Sep. 1998, 136(3):480-90 (Abstract).
Shechter et al., "Oral Magnesium Supplementation Inhibits Platelet-Dependent Thrombosis in Patients with Coronary Artery Disease", Am J. Cardiol, 1999, 84(2):152-156 (Abstract).

Weir et al., "Microvascular Disease and Dementia in the Elderly: Are they related to Hyperhomocysteinemia? 1,2", Am J Clin Nutr., 2000, pp. 859-860.

Virtamo et al., "Sereum Selenium and the Risk of Coronary Heart Disease and Stroke", Am J Epidemiol, 1985, 122(2):276-282 (Abstract).

Ford et al., "Serum Alpha-Tocopherol Status in the United States Population", Am J. Epidemiol, 1999, 150(3):290-300 (Abstract).

Conlin et al., "The Effect of Dietary Patterns on Blood Pressure Control in Hypertensive Patients", Am J Hypertens, 2000, 13(9):949-955 (Abstract).

Griffith et al., "The influence of Dietary and Nondietary Calcium Supplementation on Blood Pressure", Am J Hypertens, 1999, 12(1 pt 1):84-92 (Abstract).

Heaney, "Long-Latency Deficiency Disease: Insights from Calcium and Vitamin D 1-4", Am J Clin Nutr, 2003, 78(5):912-919.

Rochtchina et al., "Elevated Serum Homocysteine, Low Serum Vitamine B12, Folate, and Age related Macular Degeneration", Am J Ophthalmol, Feb. 2007, 143(2):344-6 (Abstract).

Penninx et al., "Vitamin B(12) Deficiency and Depression in Physically Disabled Older Womer", Am J Psychiatry, 2000, 157(5):715-721.

Tiemeier et al., "Vitamin B12, Folate, and Homocysteine in Depression: The Rotterdam Study", Am J Psychiatry, 2002, 159(12):2099-2101.

Bell et al., "S-adenosylmethionine Treatment of Depression", Am J Psychiatry, 1988, 145(9):1110-1114 (Abstract).

Plon "S-Adenosylmethionine Treatment of Depression: A Controlled Clinical Trial" Am J Psychiatry 1988; 145(9):1110-1114 (Abstract).

Miller et al., "Benefits of Diary Product Consumption on Blood Preasure in Humans: A Summary of the Bomedical Literature.", J Am Coll Nutr., 2000, 19(2Suppl):147S-164S.

Folsom et al., "Prospective Study of Coronary Heart Disease Incidence in Relation to Fasting Total Homocysteine, Related Genetic Polymorphisms, and B Vitamins: The Atherosclerosis Risk in Communities (ARIC) Study", Circulation , 1998, 98(3):204-210 (Abstract).

Higdon et al., "Niacin", Linus Pauling Institute, updated Aug. 28, 2002 (16 pages).

Higdon et al., "Sodium (Chloride)", Linus Pauling Institute, updated Dec. 2007 (22 pages).

Maas et al., "Asymmetrical Dimethylarginine (ADAM) and Coronary Endothelial Function in Patients with Coronary Disease and Mild Hypercholesterolemia", Atherosclerosis, Mar. 2007, 191(1):211-219 (Abstract).

* cited by examiner

PREVENTION OF MICRONUTRIENT DEFICIENCIES ASSOCIATED WITH COMMON DISABILITIES IN THE OVER 50 ADULT

CROSS-REFERENCE TO RELATED APPLICATIONS

The present application claims priority under 35 U.S.C. §119(e) of U.S. provisional application No. 61/026,888, filed Feb. 7, 2008, the entire disclosure whereof is expressly incorporated by reference herein.

BACKGROUND OF THE INVENTION

1. Field of the Invention

The present invention relates to the prevention of micronutrient deficiencies that are associated with common disabilities in adults which are 50 years of age or older. In particular, the present invention relates to dosage units which are suitable for preventing micronutrient deficiencies which cause or at least contribute to common disabilities in adults which are 50 years of age or older.

2. Discussion of Background Information

Results published by reputable scientific research organizations suggest that ingestion of many essential micronutrients (vitamins and minerals) by people over 50 years of age must be substantially increased over the amounts suitable for younger populations because of the relative lack of absorption and/or utilization of these essential nutrients by the aging human.

In many cases this relative lack of absorption or utilization of these critical nutrients is made even worse by inadequate availability of these nutrients in the average diet of people younger than 50 years of age. In other words, not only do many if not most people reach the age of 50 with one or more essential nutrients lacking in their diet, but this omission is aggravated by their increasing need for substantially more than is required for younger adults.

The consequences of these facts are serious. Deficiencies in micronutrients are starkly evident in virtually all of the common disabilities associated with the aging human: cognitive dysfunction ranging from mild memory loss to Alzheimer's; vision problems ranging from poor eyesight to blindness; arthritis; osteoporosis; cancer; cardiovascular disease; depression and inordinate weakness and fatigue; immune dysfunction; metabolic syndrome; muscle weakness and pain, to name but a few.

Arthritis is the leading cause of disability in the United States, limiting the activities of nearly 19 million adults. And because people are living longer, the incidence of arthritis is projected by the Division of Adult and Community Health, National Center to increase at much more rapid a rate than the rate of the increase of the population. According to this Agency, by the year 2030, the number of people with doctor-diagnosed arthritis and arthritis-attributable activity limitation will increase 34% in 50 states; increase of from 50% to 99% in 10 states; and more than a million new people will be affected each in Arizona, California, Florida, North Carolina, and Texas. Rheumatoid arthritis is an autoimmune disease, mainly characterized by inflammation of the lining, or synovium, of the joints. It can lead to long-term joint damage, resulting in chronic pain, loss of function and disability Osteopenia is defined as low bone density. Two metabolic bone diseases decrease bone mass: osteoporosis and osteomalacia. In osteoporosis, there is a decrease in bone mass with a normal ratio of bone mineral to bone matrix. In osteomalacia, the ratio of bone mineral to bone matrix is low. With osteoporosis there is an increased likelihood of fractures. The most common fractures associated with osteoporosis are fractures of the hip, fractures near the wrist and fractures of the bones of the spine.

According to a 2004 statement of the U.S. Surgeon General, no less than 10 million Americans over age 50 have osteoporosis, the most common bone disease. 34 million Americans are at risk with osteopenia. 300,000 hospitalizations occur each year due to hip fractures. 1.5 million people each year suffer a fracture from osteoporosis. 1 out of every 2 women over age 50 will have an osteoporosis related fracture in their lifetime, with risks increasing with age. Osteoporosis can occur in men as well; 6% of white men over age 50 will suffer a hip fracture.

Bone density naturally declines with age. By definition, 16% of young white women (one out of six) have osteopenia. By age 65 years about half of the women in the USA will have either osteopenia or osteoporosis, and by age 80 almost all women have had some bone loss and bone density will show either osteopenia or osteoporosis. Sustaining a hip fracture is one of the most serious consequences of osteoporosis. Nearly one third of those who sustain osteoporotic hip fractures enter nursing homes within the year following the fracture, and one person in five dies within one year of experiencing an osteoporotic hip fracture. [*National Institutes of Health. Osteoporosis Prevention, Diagnosis, and Therapy. NIH Consensus Statement.* 2000; 17(1):1-36.]

Cardiovascular disease involves any disorder of the heart and blood vessels that make up the cardiovascular system. While the term technically refers to any disease that affects the cardiovascular system, it is usually used to refer to those related to atherosclerosis (arterial disease). These conditions have similar causes, mechanisms, and treatments. Coronary heart disease occurs when blood vessels which supply the heart become clogged or blocked, increasing the risk of a heart attack. Vascular damage can also occur to blood vessels supplying the brain, and can result in a stroke. Diseases of the heart alone cause 30% of all deaths, with other diseases of the cardiovascular system causing substantial further death and disability. It is the number 1 cause of death and disability in the United States and most European countries.

A 2001 study of cognitive impairment in the elderly found that this condition may affect a significant proportion of older people. The research, which looked at cognitive difficulties falling short of Alzheimer's disease or dementia among community-dwelling residents found that nearly one in four had measurable cognitive problems. In addition, prevalence increased with age, the study finding that 38 percent of people age 85 and older had some degree of cognitive impairment short of dementia.

In addition, the U.S. National Institute on Aging estimated that up to 4.5 million Americans suffer from Alzheimer's Disease [AD]. The disease usually begins after age 60, and risk goes up with age. About 5 percent of men and women ages 65 to 74 have AD, and nearly half of those age 85 and older may have the disease. AD is a slow disease, starting with mild memory problems and ending with severe brain damage. The course the disease takes and how fast changes occur vary from person to person. On average, AD patients live from 8 to 10 years after they are diagnosed, though the disease can last for as many as 20 years.

In any given 1-year period, 9.5 percent of the population, or about 20.9 million American adults, suffer from a depressive illness. [Robins L N, Regier D A (Eds). *Psychiatric Disorders in America, The Epidemiologic Catchment Area Study*, 1990; New York: The Free Press.] Symptoms of depression include decreased energy, fatigue, and changes in mood. The economic cost for this disorder is high, but the cost in human suffering cannot be estimated. Depressive illnesses often interfere with normal functioning and cause pain and suffering not only to those who have a disorder, but also to those who care about them.

One of the major factors in failing human performance as a result of aging is the gradual weakening of the immune function. This loss is reflected in mortality figures that places death by pneumonia, chronic respiratory diseases, and certain infectious diseases as the $5^{th}$ cause of death in the general population over the age of 85. [*National Center for Health Statistics, Data Warehouse on Trends in Health and Aging*, 2007.]

Obesity is increasing rapidly throughout the world, and the incidence of obesity has nearly doubled form 1991 to 1998. [*WebMD Daily*, Sep. 7, 2007]. Obesity has reached epidemic proportions in the United States. One in three Americans is obese. Obesity is not just a cosmetic consideration; it is a dire health dilemma directly harmful to one's health. In the United States, roughly 300,000 deaths per year are directly related to obesity.

Obesity also increases the risk of developing a number of chronic diseases including: insulin resistance, type 2 (adult-onset) diabetes, high blood pressure (hypertension), high cholesterol (hypercholesterolemia), stroke (cerebrovascular accident or CVA), heart attack, congestive heart failure, cancer, gallstones, gout and gouty arthritis, osteoarthritis (degenerative arthritis) of the knees, hips, and the lower back, sleep apnea and pickwickian syndrome (obesity, red face, under-ventilation, and drowsiness).

Oxidative stress is caused by an imbalance between the production of reactive oxygen and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA. In humans, oxidative stress is involved in many diseases, such as atherosclerosis, Parkinson's disease and Alzheimer's disease and is believed to be important in ageing.

Macular degeneration is an incurable eye disease and is the leading cause of blindness for those aged 55 and older in the United States, affecting more than 10 million Americans. Macular degeneration is caused by the deterioration of the central portion of the retina, the inside back layer of the eye that records the images we see and sends them via the optic nerve from the eye to the brain. The retina's central portion, known as the macula, is responsible for focusing central vision in the eye, and it controls our ability to read, drive a car, recognize faces or colors, and see objects in fine detail. As people age their chances of developing eye diseases increase dramatically. Since many people diagnosed with macular degeneration are over age 55, the number of cases of macular degeneration in the U.S. will increase significantly as baby boomers age.

Hidden amongst the massive data available from reputable scientific research organizations on the critical role of vitamins and minerals in alleviating and even preventing most of the disabilities associated with human aging is the fact that interactions between many if not all of these micronutrients play an important role in the prevention or amelioration of most of the disabilities with which the elderly are commonly afflicted. In other words, without the proper ratios of these interactive micronutrients, one essential micronutrient (e.g., vitamin or mineral) that may be adequately supplied in the diet or by supplementation in the adult may fail to function properly because there is a deficiency of another micronutrient that the former micronutrient needs to fulfill its role.

SUMMARY OF THE INVENTION

The present invention provides a micronutrient dosage unit for ingestion by a human over a period of about 24 hours, in particular a human of age 50 and above. The dosage unit comprises two or more (e.g., at least three, at least four, at least five, at least six, at least seven, at least eight or even all) micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium. At least two (e.g., at least three, at least four, at least five, at least six, at least seven, at least eight, at least nine, at least ten or even all) of these micronutrients are present in at least one ratio within the following ranges:

(1) from about 5 IU to about 50 IU of vitamin E per 1 mg of zinc
(2) from about 0.7 mg to about 1.5 mg of vitamin $B_6$ per 1 mg of vitamin $B_2$
(3) from about 2.5 IU to about 3.6 IU of vitamin E per 1 µg of vitamin K
(4) from about 20 mg to about 40 mg of magnesium per 1 mg of boron
(5) from about 8 mg to about 12 mg of calcium per 10 IU of vitamin D
(6) from about 5 mg to about 10 mg of calcium per 1 mg of magnesium
(7) from about 0.9 mg to about 1.6 mg of magnesium per 10 IU of vitamin D
(8) from about 25 IU to about 50 IU of vitamin A per 10 IU of vitamin D
(9) from about 50 IU to about 100 IU of vitamin A per 1 mg of Zn
(10) from about 3 IU to about 10 IU of vitamin A per 1 IU of vitamin E
(11) from about 1.2 µg to about 1.9 µg of vitamin $B_9$ per 1 µg of vitamin $B_{12}$
(12) from about 15 IU to about 30 IU of vitamin A per 1 µg of vitamin K
(13) from about 0.1 µg to about 0.8 µg of chromium per 1 mg of vitamin C
(14) from about 3.5 mg to about 6.5 mg of vitamin $B_6$ per 1 mg of vitamin $B_9$
(15) from about 20 µg to about 60 µg of boron per 10 IU of vitamin D.

In one aspect of the dosage unit, at least two (e.g., at least three, at least four, at least five, at least six, at least seven, at least eight, at least nine, at least ten or even all) of these micronutrients may be present in at least one ratio within the following ranges:

(1') from about 7 IU to about 30 IU of vitamin E per 1 mg of zinc
(2') from about 0.8 mg to about 1.3 mg of vitamin $B_6$ per 1 mg of vitamin $B_2$
(3') from about 2.8 IU to about 3.5 IU of vitamin E per 1 µg of vitamin K
(4') from about 25 mg to about 35 mg of magnesium per 1 mg of boron
(5') from about 9 mg to about 10 mg of calcium per 10 IU of vitamin D
(6') from about 6 mg to about 9 mg of calcium per 1 mg of magnesium (7') from about 1.0 mg to about 1.5 mg of magnesium per 10 IU of vitamin D
(8') from about 30 IU to about 45 IU of vitamin A per 10 IU of vitamin D
(9') from about 60 IU to about 90 IU of vitamin A per 1 mg of Zn
(10') from about 5 IU to about 9 IU of vitamin A per 1 IU of vitamin E
(11') from about 1.25 μg to about 1.8 μg of vitamin $B_9$ per 1 μg of vitamin $B_{12}$
(12') from about 20 IU to about 28 IU of vitamin A per 1 μg of vitamin K
(13') from about 0.2 μg to about 0.7 μg of chromium per 1 mg of vitamin C
(14') from about 4 mg to about 6 mg of vitamin $B_6$ per 1 mg of vitamin $B_9$
(15') from about 25 μg to about 55 μg of boron per 10 IU of vitamin D.

In another aspect of the dosage unit, at least two (e.g., at least three, at least four, at least five, at least six, at least seven, at least eight, at least nine, at least ten or even all) of these micronutrients may be present in at least one ratio within the following ranges:
(1") from about 8 IU to about 15 IU of vitamin E per 1 mg of zinc
(2") from about 0.9 mg to about 1.2 mg of vitamin $B_6$ per 1 mg of vitamin $B_2$
(3") from about 3.0 IU to about 3.4 IU of vitamin E per 1 μg of vitamin K
(4") from about 28 mg to about 33 mg of magnesium per 1 mg of boron
(5") from about 9.2 mg to about 9.7 mg of calcium per 10 IU of vitamin D
(6") from about 7 mg to about 8.5 mg of calcium per 1 mg of magnesium
(7") from about 1.1 mg to about 1.4 mg of magnesium per 10 IU of vitamin D
(8") from about 33 IU to about 40 IU of vitamin A per 10 IU of vitamin D
(9") from about 70 IU to about 80 IU of vitamin A per 1 mg of Zn
(10") from about 6.5 IU to about 8.5 IU of vitamin A per 1 IU of vitamin E
(11") from about 1.3 μg to about 1.7 μg of vitamin $B_9$ per 1 μg of vitamin $B_{12}$
(12") from about 24 IU to about 26 IU of vitamin A per 1 μg of vitamin K
(13") from about 0.3 μg to about 0.6 μg of chromium per 1 mg of vitamin C
(14") from about 4.5 mg to about 5.5 mg of vitamin $B_6$ per 1 mg of vitamin $B_9$
(15") from about 30 μg to about 50 μg of boron per 10 IU of vitamin D.

In yet another aspect, micronutrients may be present in the dosage unit in at least five (e.g., at least six, at least seven or even all) ratios within the above ranges (1") to (7") and (11"), in particular, in at least five (e.g., at least six or all) ratios within the above ranges (1"), (3") to (7") and (11").

In another aspect, the 24-hour dosage unit may comprise one or more (e.g., at least three, at least four, at least five, at least six, at least seven, at least eight, at least nine, at least ten or even all) of:
(a) from about 1000 to about 3500 IU of vitamin A
(b) from about 2 mg to about 5.5 mg of vitamin $B_2$
(c) from about 2.5 mg to about 6 mg of vitamin $B_6$
(d) from about 400 μg to about 1000 μg of vitamin $B_9$
(e) from about 250 μg to about 750 μg of vitamin $B_{12}$
(f) from about 200 mg to about 2,000 mg of vitamin C
(g) from about 300 IU to about 1000 IU of vitamin D
(h) from about 200 IU to about 700 IU of vitamin E
(i) from about 80 μg to about 200 μg of vitamin K
(j) from about 600 mg to about 900 mg of calcium
(k) from about 50 mg to about 150 mg of magnesium
(l) from about 10 mg to about 60 mg of zinc
(m) from about 2 mg to about 6 mg of boron
(n) from about 100 μg to about 300 μg of chromium,
and/or may comprise one or more (e.g., at least three, at least four, at least five, at least six, at least seven, at least eight, at least nine, at least ten or even all) of:
(a') from about 1500 to about 3200 IU of vitamin A
(b') from about 2.5 mg to about 5 mg of vitamin $B_2$
(c') from about 3 mg to about 5 mg of vitamin $B_6$
(d') from about 600 μg to about 900 μg of vitamin $B_9$
(e') from about 350 μg to about 700 μg of vitamin $B_{12}$
(f') from about 300 mg to about 1800 mg of vitamin C
(g') from about 400 IU to about 900 IU of vitamin D
(h') from about 300 IU to about 600 IU of vitamin E
(i') from about 100 μg to about 170 μg of vitamin K
(j') from about 650 mg to about 850 mg of calcium
(k') from about 70 mg to about 130 mg of magnesium
(l') from about 20 mg to about 50 mg of zinc
(m') from about 2.5 mg to about 4.5 mg of boron
(n') from about 120 μg to about 270 μg of chromium,
and/or may comprise one or more (e.g., at least three, at least four, at least five, at least six, at least seven, at least eight, at least nine, at least ten or even all) of:
(a") from about 1800 to about 3000 IU of vitamin A
(b") from about 3 mg to about 4.5 mg of vitamin $B_2$
(c") from about 3.5 mg to about 4.5 mg of vitamin $B_6$
(d") from about 700 μg to about 850 μg of vitamin $B_9$
(e") from about 500 μg to about 650 μg of vitamin $B_{12}$
(f") from about 350 mg to about 1600 mg of vitamin C
(g") from about 500 IU to about 850 IU of vitamin D
(h") from about 350 IU to about 500 IU of vitamin E
(i") from about 110 μg to about 150 μg of vitamin K
(j") from about 700 mg to about 800 mg of calcium
(k") from about 80 mg to about 120 mg of magnesium
(l") from about 25 mg to about 45 mg of zinc
(m") from about 2.8 mg to about 4 mg of boron
(n") from about 150 μg to about 250 μg of chromium.

In yet another aspect, the dosage unit may comprise at least six (e.g, at least seven, at least eight, at least nine or even all) micronutrients selected from vitamin $B_2$, vitamin $B_6$, vitamin $B_9$, vitamin $B_{12}$, vitamin D, vitamin K, calcium, magnesium, zinc and boron, for example, at least four (e.g, at least five or even all) micronutrients selected from vitamin $B_6$, vitamin $B_9$, vitamin $B_{12}$, vitamin D, calcium and magnesium.

In a still further aspect, the dosage unit of the present invention may comprise from about 550 μg to about 650 μg of vitamin $B_{12}$ for a period of 24 hours and/or may comprise from about 1.2 μg to about 1.5 μg of vitamin $B_9$ per 1 μg of vitamin $B_{12}$.

In another aspect, the dosage unit may further comprise one of more of vitamin $B_1$, vitamin $B_3$, vitamin $B_5$, vitamin $B_7$, lycopene, lutein, zeaxanthin, copper, iodine, manganese, vanadium, molybendum, nickel, silicon and selenium. For example, the dosage unit may comprise, for a period of 24 hours, one or more (e.g., at least two, at least three, at least four, at least five or at least six) of:
(o) from about 4 mg to about 35 mg of vitamin $B_3$
(p) from about 2 mg to about 20 mg of lutein
(q) from about 2 mg to about 25 mg of zeaxanthin
(r) from about 5 μg to about 300 μg of nickel
(s) from about 2 mg to about 25 mg of silicon (t) from about 25 µg to about 300 µg of selenium
(u) from about 0.5 mg to about 5 mg of vitamin $B_1$
(v) from about 1 mg to about 25 mg of vitamin $B_5$
(w) from about 10 µg to about 0.1 mg of vitamin $B_7$
(x) from about 2 mg to about 25 mg of lycopene
(y) from about 30 µg to about 0.2 mg of iodine
(z) from about 1 mg to about 4 mg of manganese
(aa) from about 2 µg to about 50 µg of vanadium
(bb) from about 15 µg to about 1.5 mg of molybdenum
(cc) from about 0.5 mg to about 10 mg of copper,
and/or one or more (e.g., at least two, at least three, at least four, at least five or at least six) of:
(o') from about 15 mg to about 25 mg of vitamin $B_3$
(p') from about 3 mg to about 15 mg of lutein
(q') from about 5 mg to about 20 mg of zeaxanthin
(r') from about 100 µg to about 200 µg of nickel
(s') from about 3 mg to about 15 mg of silicon
(t') from about 50 µg to about 250 µg of selenium
(u') from about 1 mg to about 3 mg of vitamin $B_1$
(v') from about 3 mg to about 15 mg of vitamin $B_5$
(w') from about 25 µg to about 90 µg of vitamin $B_7$
(x') from about 3 mg to about 15 mg of lycopene
(y') from about 50 µg to about 150 µg of iodine
(z') from about 1.5 mg to about 3 mg of manganese
(aa') from about 5 µg to about 20 µg of vanadium
(bb') from about 25 µg to about 0.1 mg of molybdenum
(cc') from about 1 mg to about 8 mg of copper,
and/or one or more (e.g., at least two, at least three, at least four, at least five or at least six) of:
(o") from about 18 mg to about 22 mg of vitamin $B_3$
(p") from about 5 mg to about 8 mg of lutein
(q") from about 8 mg to about 15 mg of zeaxanthin
(r") from about 130 µg to about 170 µg of nickel
(s") from about 4 mg to about 10 mg of silicon
(t") from about 150 µg to about 220 µg of selenium
(u") from about 1.5 mg to about 2.5 mg of vitamin $B_1$
(v") from about 4 mg to about 10 mg of vitamin $B_5$
(w") from about 40 µg to about 85 µg of vitamin $B_7$
(x") from about 4 mg to about 10 mg of lycopene
(y") from about 70 µg to about 130 µg of iodine
(z") from about 1.8 mg to about 2.5 mg of manganese
(aa") from about 7 µg to about 15 µg of vanadium
(bb") from about 35 µg to about 70 µg of molybdenum
(cc") from about 1.5 mg to about 5 mg of copper.

In another aspect, the dosage unit of the present invention may comprise at least 15 (e.g., at least 16 or even all) micronutrients selected from vitamin $B_2$, vitamin $B_3$, vitamin $B_6$, vitamin $B_9$, vitamin $B_{12}$, vitamin D, vitamin K, lutein, zeaxanthin, calcium, magnesium, chromium, nickel, zinc, boron, silicon and selenium, e.g., it may comprise at least vitamin $B_2$, vitamin $B_3$, vitamin $B_6$, vitamin $B_9$, vitamin $B_{12}$, vitamin D, vitamin K, lutein, zeaxanthin, calcium, magnesium chromium, nickel, zinc, boron, silicon and selenium. For example, this dosage unit may comprise one or more (e.g., at least two, at least three, at least four, at least five, at least six, at least seven, at least eight or even all) of vitamin $B_1$, vitamin $B_5$, vitamin $B_7$, lycopene, iodine, manganese, vanadium, molybdenum and copper.

In another aspect, the dosage unit may be substantially free of phosphorus and/or it may be substantially free of iron.

In another aspect, the dosage unit of the present invention may be divided into at least two subunits and/or may comprise a solid dosage form, e.g., one or more of a tablet, a capsule and a caplet.

In another aspect, the dosage unit of the present invention may be for preventing or treating cardiovascular diseases and may comprise at least vitamin $B_2$, vitamin $B_6$, vitamin $B_9$, vitamin $B_{12}$, vitamin C, vitamin D, vitamin E, vitamin K, calcium, magnesium, zinc, boron, chromium, selenium and copper. For example, the 24-hour dosage unit may comprise from about 100 µg to about 200 µg of selenium and/or from about 450 µg to about 900 µg of copper in addition to one more (e.g., all) of the amounts (b) to (n) set forth above.

In another aspect, the dosage unit of the present invention may be for preventing or treating cognitive impairment and may comprise at least vitamin A, vitamin $B_2$, vitamin $B_6$, vitamin $B_9$, vitamin $B_{12}$, vitamin C, vitamin E, vitamin K, magnesium, zinc, boron, iodine, selenium and manganese. For example, the 24-hour dosage unit may comprise from about 100 µg to about 200 µg of selenium and/or from about 1 mg to about 2 mg of manganese and/or from about 75 µg to about 150 µg of iodine in addition to one more (e.g., all) of the amounts (a) to (f), (h), (i) and (k) to (m) set forth above.

In another aspect, the dosage unit of the present invention may be for preventing or treating cancer and may comprise at least vitamin $B_6$, vitamin $B_9$, vitamin $B_{12}$, vitamin C, vitamin D, vitamin E, calcium, magnesium, zinc, boron, copper, selenium, vitamin $B_3$, lutein and lycopene. For example, the 24-hour dosage unit may comprise (i) from about 100 µg to about 200 µg of selenium and/or (ii) from about 450 µg to about 900 µg of copper and/or (iii) from about 10 mg to about 20 mg of vitamin $B_3$ and/or (iv) from about 15 mg to about 30 mg of lycopene and/or (v) from about 5 mg to about 10 mg of lutein in addition to one or more (e.g., all) of the amounts (c) to (h) and (j) to (m) set forth above.

In another aspect, the dosage unit of the present invention may be for preventing or treating depression and/or fatigue and/or loss of energy and may comprise at least vitamin $B_2$, vitamin $B_6$, vitamin $B_9$, vitamin $B_{12}$, vitamin C, vitamin D, calcium, magnesium, boron and copper. For example, the 24-hour dosage unit may comprise from about 450 µg to about 900 µg of copper in addition to one or more (e.g., all) of the amounts (b) to (g), (j), (k) and (m) set forth above.

In another aspect, the dosage unit of the present invention may be for preventing or treating a loss of the immune function and may comprise at least vitamin A, vitamin $B_2$, vitamin $B_6$, vitamin D, vitamin E, vitamin K, zinc, boron, selenium and copper. For example, the 24-hour dosage unit may comprise from about 100 µg to about 200 µg of selenium and/or from about 450 µg to about 900 µg of copper in addition to one or more (e.g., all) of the amounts (a) to (c), (g) to (i), (l) and (m) set forth above.

In another aspect, the dosage unit of the present invention may be for preventing or treating metabolic syndrome and may comprise at least vitamin C, vitamin D, vitamin E, vitamin $B_7$, magnesium, zinc, manganese and chromium. For example, the 24-hour dosage unit may comprise from about 1 mg to about 2 mg of manganese and/or from about 15 µg to about 30 µg of vitamin $B_7$ in addition to one or more (e.g., all) of the amounts (f) to (h), (k) and (l) set forth above.

In another aspect, the dosage unit of the present invention may be for use in a method of preventing or treating osteopenia and may comprise at least vitamin A, vitamin D, vitamin K, calcium, magnesium, zinc, boron, manganese and copper. For example, the 24-hour dosage unit may comprise from about 450 µg to about 900 µg of copper and/or from about 1 mg to about 2 mg of manganese in addition to one or more (e.g., all) of the amounts (a), (g) and (i) to (m) set forth above.

In another aspect, the dosage unit of the present invention may be for preventing or treating arthritis and may comprise at least vitamin $B_2$, vitamin D, magnesium, boron and copper. For example, the 24-hour dosage unit may comprise from about 450 µg to about 900 µg of copper in addition to one or more (e.g., all) of the amounts (b), (g), (k) and (m) set forth above.

In another aspect, the dosage unit of the present invention may be for preventing or treating muscle weakness and may comprise at least vitamin $B_9$, vitamin $B_{12}$, vitamin D, vitamin E, vitamin K, calcium, magnesium, zinc and boron.

In another aspect, the dosage unit of the present invention may be for preventing or treating obesity and may comprise at least vitamin D, calcium, magnesium and boron.

In another aspect, the dosage unit of the present invention may be for preventing or treating inflammatory processes and may comprise at least vitamin E, vitamin K, zinc and boron.

In another aspect, the dosage unit of the present invention may be for preventing or treating oxidative stress and may comprise at least vitamin $B_1$, vitamin $B_2$, vitamin $B_3$, vitamin $B_6$, vitamin C, vitamin E, vitamin K, magnesium, zinc, selenium, copper and manganese. For example, the 24-hour dosage unit may comprise from about 100 µg to about 200 µg of selenium and/or from about 1 mg to about 2 mg of manganese and/or from about 1 mg to about 2 mg of vitamin $B_1$ and/or from about 10 mg to about 20 mg of vitamin $B_3$ and/or from about 450 µg to about 900 µg of copper in addition to one or more (e.g., all) of the amounts (b), (c), (f), (h), (i) and (k) set forth above.

In another aspect, the dosage unit of the present invention may be for promoting wound healing and may comprise at least calcium, magnesium, copper and manganese. For example, the 24-hour dosage unit may comprise from about 450 µg to about 900 µg of copper and/or from about 1 mg to about 2 mg of manganese in addition to one or both of the amounts (j) and (k) set forth above.

In another aspect, the dosage unit of the present invention may be for preventing or treating impaired vision and may comprise at least vitamin A, vitamin $B_2$, vitamin $B_6$, vitamin $B_9$, vitamin $B_{12}$, vitamin C, vitamin D, vitamin E, calcium, magnesium, zinc, boron, lutein and zeaxanthin. For example, the 24-hour dosage unit may comprise from about 5 mg to about 10 mg of lutein and/or from about 5 mg to about 10 mg of zeaxanthine in addition to one or more (e.g., all) of the amounts (a) to (h) and (j) to (m) set forth above. In another aspect, this dosage unit may further comprise lycopene.

In another aspect, the dosage unit of the present invention may be for use in combination with a food supplement for preventing and/or treating macular degeneration, and may be substantially free of vitamin A, vitamin E, zinc and copper (i.e., may not comprise more than trace amounts of these micronutrients).

The present invention also provides a method of at least one of preventing and alleviating in a human one or more conditions which are caused or aggravated by inadequate intake of micronutrients. The method comprises providing to a subject in need thereof two or more (e.g., at least three, at least four, at least five, at least six, at least seven, at least eight or even all) micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium. The micronutrients are provided in relative amounts which will result in ingestion over a 24-hour period of one or more of:

(1) from about 5 IU to about 50 IU of vitamin E per 1 mg of zinc
(2) from about 0.7 mg to about 1.5 mg of vitamin $B_6$ per 1 mg of vitamin $B_2$
(3) from about 2.5 IU to about 3.6 IU of vitamin E per 1 µg of vitamin K
(4) from about 20 mg to about 40 mg of magnesium per 1 mg of boron
(5) from about 8 mg to about 12 mg of calcium per 10 IU of vitamin D
(6) from about 5 mg to about 10 mg of calcium per 1 mg of magnesium
(7) from about 0.9 mg to about 1.6 mg of magnesium per 10 IU of vitamin D
(8) from about 25 IU to about 50 IU of vitamin A per 10 IU of vitamin D
(9) from about 50 IU to about 100 IU of vitamin A per 1 mg of Zn
(10) from about 3 IU to about 10 IU of vitamin A per 1 IU of vitamin E
(11) from about 1.2 µg to about 1.9 µg of vitamin $B_9$ per 1 µg of vitamin $B_{12}$
(12) from about 15 IU to about 30 IU of vitamin A per 1 µg of vitamin K
(13) from about 0.1 µg to about 0.8 µg of chromium per 1 mg of vitamin C
(14) from about 3.5 mg to about 6.5 mg of vitamin $B_6$ per 1 mg of vitamin $B_9$
(15) from about 20 µg to about 60 µg of boron per 10 IU of vitamin D,
and/or one or more of:
(1') from about 7 IU to about 30 IU of vitamin E per 1 mg of zinc
(2') from about 0.8 mg to about 1.3 mg of vitamin $B_6$ per 1 mg of vitamin $B_2$
(3') from about 2.8 IU to about 3.5 IU of vitamin E per 1 µg of vitamin K
(4') from about 25 mg to about 35 mg of magnesium per 1 mg of boron
(5') from about 9 mg to about 10 mg of calcium per 10 IU of vitamin D
(6') from about 6 mg to about 9 mg of calcium per 1 mg of magnesium
(7') from about 1.0 mg to about 1.5 mg of magnesium per 10 IU of vitamin D
(8') from about 30 IU to about 45 IU of vitamin A per 10 IU of vitamin D
(9') from about 60 IU to about 90 IU of vitamin A per 1 mg of Zn
(10') from about 5 IU to about 9 IU of vitamin A per 1 IU of vitamin E
(11') from about 1.25 µg to about 1.8 µg of vitamin $B_9$ per 1 µg of vitamin $B_{12}$
(12') from about 20 IU to about 28 IU of vitamin A per 1 µg of vitamin K
(13') from about 0.2 µg to about 0.7 µg of chromium per 1 mg of vitamin C
(14') from about 4 mg to about 6 mg of vitamin $B_6$ per 1 mg of vitamin $B_9$
(15') from about 25 µg to about 55 µg of boron per 10 IU of vitamin D,
and/or one or more of:
(1") from about 8 IU to about 15 IU of vitamin E per 1 mg of zinc
(2") from about 0.9 mg to about 1.2 mg of vitamin $B_6$ per 1 mg of vitamin $B_2$
(3") from about 3.0 IU to about 3.4 IU of vitamin E per 1 µg of vitamin K
(4") from about 28 mg to about 33 mg of magnesium per 1 mg of boron
(5") from about 9.2 mg to about 9.7 mg of calcium per 10 IU of vitamin D (6") from about 7 mg to about 8.5 mg of calcium per 1 mg of magnesium
(7") from about 1.1 mg to about 1.4 mg of magnesium per 10 IU of vitamin D
(8") from about 33 IU to about 40 IU of vitamin A per 10 IU of vitamin D
(9") from about 70 IU to about 80 IU of vitamin A per 1 mg of Zn
(10") from about 6.5 IU to about 8.5 IU of vitamin A per 1 IU of vitamin E
(11") from about 1.3 µg to about 1.7 µg of vitamin $B_9$ per 1 µg of vitamin $B_{12}$
(12") from about 24 IU to about 26 IU of vitamin A per 1 µg of vitamin K
(13") from about 0.3 µg to about 0.6 µg of chromium per 1 mg of vitamin C
(14") from about 4.5 mg to about 5.5 mg of vitamin $B_6$ per 1 mg of vitamin $B_9$
(15") from about 30 µg to about 50 µg of boron per 10 IU of vitamin D.

In one aspect of the method, the subject may be directed to ingest the two or more micronutrients over a 24-hour period in amounts within one or more of the following ranges:
(a) from about 1000 to about 3500 IU of vitamin A
(b) from about 2 mg to about 5.5 mg of vitamin $B_2$
(c) from about 2.5 mg to about 6 mg of vitamin $B_6$
(d) from about 400 µg to about 1000 µg of vitamin $B_9$
(e) from about 250 µg to about 750 µg of vitamin $B_{12}$
(f) from about 200 mg to about 2,000 mg of vitamin C
(g) from about 300 IU to about 1000 IU of vitamin D
(h) from about 200 IU to about 700 IU of vitamin E
(i) from about 80 µg to about 200 µg of vitamin K
(j) from about 600 mg to about 900 mg of calcium
(k) from about 50 mg to about 150 mg of magnesium
(l) from about 10 mg to about 60 mg of zinc
(m) from about 2 mg to about 6 mg of boron
(n) from about 100 µg to about 300 µg of chromium,
and/or in one or more amounts within the following ranges:
(a') from about 1500 to about 3200 IU of vitamin A
(b') from about 2.5 mg to about 5 mg of vitamin $B_2$
(c') from about 3 mg to about 5 mg of vitamin $B_6$
(d') from about 600 µg to about 900 µg of vitamin $B_9$
(e') from about 350 µg to about 700 µg of vitamin $B_{12}$
(f') from about 300 mg to about 1800 mg of vitamin C
(g') from about 400 IU to about 900 IU of vitamin D
(h') from about 300 IU to about 600 IU of vitamin E
(i') from about 100 µg to about 170 µg of vitamin K
(j') from about 650 mg to about 850 mg of calcium
(k') from about 70 mg to about 130 mg of magnesium
(l') from about 20 mg to about 50 mg of zinc
(m') from about 2.5 mg to about 4.5 mg of boron
(n') from about 120 µg to about 270 µg of chromium,
and/or in one or more amounts within the following ranges:
(a") from about 1800 to about 3000 IU of vitamin A
(b") from about 3 mg to about 4.5 mg of vitamin $B_2$
(c") from about 3.5 mg to about 4.5 mg of vitamin $B_6$
(d") from about 700 µg to about 850 µg of vitamin $B_9$
(e") from about 500 µg to about 650 µg of vitamin $B_{12}$
(f") from about 350 mg to about 1600 mg of vitamin C
(g") from about 500 IU to about 850 IU of vitamin D
(h") from about 350 IU to about 500 IU of vitamin E
(i") from about 110 µg to about 150 µg of vitamin K
(j") from about 700 mg to about 800 mg of calcium
(k") from about 80 mg to about 120 mg of magnesium
(l") from about 25 mg to about 45 mg of zinc
(m") from about 2.8 mg to about 4 mg of boron
(n") from about 150 µg to about 250 µg of chromium.

In another aspect of the method, the subject may be provided with at least 15 (or even all) micronutrients selected from vitamin $B_2$, vitamin $B_3$, vitamin $B_6$, vitamin $B_9$, vitamin $B_{12}$, vitamin D, vitamin K, lutein, zeaxanthin, calcium, magnesium chromium, nickel, zinc, boron, silicon and selenium. For example, in the case of vitamin $B_3$, lutein, zeaxanthin, nickel, silicon and selenium, if employed, the subject may be directed to ingest one or more of these micronutrients over a 24-hour period in an amount within one or more of the following ranges:
(o) from about 4 mg to about 35 mg of vitamin $B_3$
(p) from about 2 mg to about 20 mg of lutein
(q) from about 2 mg to about 25 mg of zeaxanthin
(r) from about 5 µg to about 300 µg of nickel
(s) from about 2 mg to about 25 mg of silicon
(t) from about 25 µg to about 300 µg of selenium,
and/or in an amount within one or more of the following ranges:
(o') from about 15 mg to about 25 mg of vitamin $B_3$
(p') from about 3 mg to about 15 mg of lutein
(q') from about 5 mg to about 20 mg of zeaxanthin
(r') from about 100 µg to about 200 µg of nickel
(s') from about 3 mg to about 15 mg of silicon
(t') from about 50 µg to about 250 µg of selenium,
and/or in an amount within one or more of the following ranges:
(o") from about 18 mg to about 22 mg of vitamin $B_3$
(p") from about 5 mg to about 8 mg of lutein
(q") from about 8 mg to about 15 mg of zeaxanthin
(r") from about 130 µg to about 170 µg of nickel
(s") from about 4 mg to about 10 mg of silicon
(t") from about 150 µg to about 220 µg of selenium.

In another aspect of the method of the present invention, the subject may be provided with at least one of vitamin $B_1$, vitamin $B_5$, vitamin $B_7$, lycopene, iodine, manganese, vanadium, molybdenum and copper. For example, the subject may be directed to ingest at least one of vitamin $B_1$, vitamin $B_5$, vitamin $B_7$, lycopene, iodine, manganese, vanadium, molybdenum and copper, if employed at all, over a 24-hour period in an amount within one or more of the following ranges:
(u) from about 0.5 mg to about 5 mg of vitamin $B_1$
(v) from about 1 mg to about 25 mg of vitamin $B_5$
(w) from about 10 µg to about 0.1 mg of vitamin $B_7$
(x) from about 2 mg to about 25 mg of lycopene
(y) from about 30 µg to about 0.2 mg of iodine
(z) from about 1 mg to about 4 mg of manganese
(aa) from about 2 µg to about 50 µg of vanadium
(bb) from about 15 µg to about 1.5 mg of molybdenum
(cc) from about 0.5 mg to about 10 mg of copper,
and/or in an amount within one or more of the following ranges:
(u') from about 1 mg to about 3 mg of vitamin $B_1$
(v') from about 3 mg to about 15 mg of vitamin $B_5$
(w') from about 25 µg to about 90 µg of vitamin $B_7$
(x') from about 3 mg to about 15 mg of lycopene
(y') from about 50 µg to about 150 µg of iodine
(z') from about 1.5 mg to about 3 mg of manganese
(aa') from about 5 µg to about 20 µg of vanadium
(bb') from about 25 µg to about 0.1 mg of molybdenum
(cc') from about 1 mg to about 8 mg of copper,
and/or in an amount within one or more of the following ranges:
(u") from about 1.5 mg to about 2.5 mg of vitamin $B_1$
(v") from about 4 mg to about 10 mg of vitamin $B_5$
(w") from about 40 µg to about 85 µg of vitamin $B_7$
(x") from about 4 mg to about 10 mg of lycopene
(y") from about 70 µg to about 130 µg of iodine (z") from about 1.8 mg to about 2.5 mg of manganese
(aa") from about 7 µg to about 15 µg of vanadium
(bb") from about 35 µg to about 70 µg of molybdenum
(cc") from about 1.5 mg to about 5 mg of copper.

In another aspect of the instant method, the subject may be at least about 50 years (e.g., at least about 55 years or at least about 60 years) old.

In yet another aspect, the method of the present invention may comprise directing the subject to ingest the dosage unit of the present invention as set forth above (including the various aspects thereof).

In another aspect, the method of the present invention may be for the prevention or alleviation of cardiovascular diseases and may comprise providing a subject in need thereof with micronutrients which comprise at least vitamin $B_2$, vitamin $B_6$, vitamin $B_9$, vitamin $B_{12}$, vitamin C, vitamin D, vitamin E, vitamin K, calcium, magnesium, zinc, boron, chromium, selenium and copper. For example, the subject may be directed to ingest selenium over a 24-hour period in an amount of from about 100 µg to about 200 µg and/or may be directed to ingest copper in an amount of from about 450 µg to about 900 µg in addition to one more (e.g., all) of the remaining micronutrients in the amounts (b) to (n) set forth above.

In another aspect, the method of the present invention may be for the prevention or alleviation of cognitive impairment, wherein the method comprises providing a subject in need thereof with micronutrients which comprise at least vitamin A, vitamin $B_2$, vitamin $B_6$, vitamin $B_9$, vitamin $B_{12}$, vitamin C, vitamin E, vitamin K, magnesium, zinc, boron, iodine, selenium and manganese. For example, the subject may be directed to ingest over a 24-hour period from about 100 µg to about 200 µg of selenium and/or from about 1 mg to about 2 mg of manganese and/or from about 75 µg to about 150 µg of iodine in addition to one more (e.g., all) of the amounts (a) to (f), (h), (i) and (k) to (m) set forth above.

In another aspect, the method of the present invention may be for the prevention or treatment of cancer and may comprise providing a subject in need thereof with micronutrients which comprise at least vitamin $B_6$, vitamin $B_9$, vitamin $B_{12}$, vitamin C, vitamin D, vitamin E, calcium, magnesium, zinc, boron, copper, selenium, vitamin $B_3$, lutein and lycopene. For example, the subject may be directed to ingest over a 24-hour period from about 100 µg to about 200 µg of selenium and/or from about 450 µg to about 900 µg of copper and/or from about 10 mg to about 20 mg of vitamin $B_3$ and/or from about 15 mg to about 30 mg of lycopene and/or from about 5 mg to about 10 mg of lutein in addition to one or more (e.g., all) of the amounts (c) to (h) and (j) to (m) set forth above.

In another aspect, the method of the present invention may be for the prevention or alleviation of depression and/or fatigue and/or loss of energy and may comprise providing a subject in need thereof with micronutrients which comprise at least vitamin $B_2$, vitamin $B_6$, vitamin $B_9$, vitamin $B_{12}$, vitamin C, vitamin D, calcium, magnesium, boron and copper. For example, the subject may be directed to ingest over a 24-hour period from about 450 µg to about 900 µg of copper in addition to one or more (e.g., all) of the amounts (b) to (g), (j), (k) and (m) set forth above.

In another aspect, the method of the present invention may be for the prevention or alleviation of a loss of the immune function and may comprise providing a subject in need thereof with micronutrients which comprise at least vitamin A, vitamin $B_2$, vitamin $B_6$, vitamin D, vitamin E, vitamin K, zinc, boron, selenium and copper. For example, the subject may be directed to ingest over a 24-hour period from about 100 µg to about 200 µg of selenium and/or from about 450 µg to about 900 µg of copper in addition to one or more (e.g., all) of the amounts (a) to (c), (g) to (i), (l) and (m) set forth above.

In another aspect, the method of the present invention may be for the prevention or alleviation of metabolic syndrome and may comprise providing a subject in need thereof with micronutrients which comprise at least vitamin C, vitamin D, vitamin E, vitamin $B_7$, magnesium, zinc, manganese and chromium. For example, the subject may be directed to ingest over a 24-hour period from about 1 mg to about 2 mg of manganese, and/or from about 15 µg to about 30 µg of vitamin $B_7$ in addition to one or more (e.g., all) of the amounts (f) to (h), (k) and (l) set forth above.

In another aspect, the method of the present invention may be for the prevention or alleviation of osteopenia and may comprise providing a subject in need thereof with micronutrients which comprise at least vitamin A, vitamin D, vitamin K, calcium, magnesium, zinc, boron, manganese and copper. For example, the subject may be directed to ingest over a 24-hour period from about 450 µg to about 900 µg of copper and/or from about 1 mg to about 2 mg of manganese in addition to one or more (e.g., all) of the amounts (a), (g) and (i) to (m) set forth above.

In another aspect, the method of the present invention may be for the prevention or alleviation of arthritis and may comprise providing a subject in need thereof with micronutrients which comprise at least vitamin $B_2$, vitamin D, magnesium, boron and copper. For example, the subject may be directed to ingest over a 24-hour period from about 450 µg to about 900 µg of copper in addition to one or more (e.g., all) of the amounts (b), (g), (k) and (m) set forth above.

In another aspect, the method of the present invention may be for the prevention or alleviation of muscle weakness and may comprise providing a subject in need thereof with micronutrients which comprise at least vitamin $B_9$, vitamin $B_{12}$, vitamin D, vitamin E, vitamin K, calcium, magnesium, zinc and boron.

In another aspect, the method of the present invention may be for the prevention or alleviation of obesity and may comprise providing a subject in need thereof with micronutrients which comprise at least vitamin D, calcium, magnesium and boron.

In another aspect, the method of the present invention may be for the prevention or alleviation of inflammatory processes and may comprise providing a subject in need thereof with micronutrients which comprise at least vitamin E, vitamin K, zinc and boron.

In another aspect, the method of the present invention may be for the prevention or alleviation of oxidative stress and may comprise providing a subject in need thereof with micronutrients which comprise at least vitamin $B_1$, vitamin $B_2$, vitamin $B_3$, vitamin $B_6$, vitamin C, vitamin E, vitamin K, magnesium, zinc, selenium, copper and manganese. For example, the subject may be directed to ingest over a 24-hour period from about 100 µg to about 200 µg of selenium and/or from about 1 mg to about 2 mg of manganese and/or from about 1 mg to about 2 mg of vitamin $B_1$ and/or from about 10 mg to about 20 mg of vitamin $B_3$ and/or from about 450 µg to about 900 µg of copper in addition to one or more (e.g., all) of the amounts (b), (c), (f), (h), (i) and (k) set forth above.

In another aspect, the method of the present invention may be for promoting wound healing and may comprise providing a subject in need thereof with micronutrients which comprise at least calcium, magnesium, copper and manganese. For example, the subject may be directed to ingest over a 24-hour period from about 450 µg to about 900 µg of copper and/or from about 1 mg to about 2 mg of manganese in addition to one or both of the amounts (j) and (k) set forth above.

In another aspect, the method of the present invention may be for the prevention or alleviation of impaired vision and may comprise providing a subject in need thereof with micronutrients which comprise at least vitamin A, vitamin $B_2$, vitamin $B_6$, vitamin $B_9$, vitamin $B_{12}$, vitamin C, vitamin D, vitamin E, calcium, magnesium, zinc, boron, lutein and zeaxanthin. For example, the subject may be directed to ingest over a 24-hour period from about 5 mg to about 10 mg of lutein and/or from about 5 mg to about 10 mg of zeaxanthine in addition to one or more (e.g., all) of the amounts (a) to (h) and (j) to (m) set forth above. In another example, the subject may be further provided with lycopene.

The present invention also provides a method of increasing the efficacy and/or the safety of two or more (e.g., at least three, at least four, at least five, at least six, at least seven, at least eight or even all) micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium in a subject in need thereof, wherein the method comprises providing the two or more micronutrients in one or more ratios within the following ranges (1) to (15):

(1) from about 5 IU to about 50 IU of vitamin E per 1 mg of zinc
(2) from about 0.7 mg to about 1.5 mg of vitamin $B_6$ per 1 mg of vitamin $B_2$
(3) from about 2.5 IU to about 3.6 IU of vitamin E per 1 µg of vitamin K
(4) from about 20 mg to about 40 mg of magnesium per 1 mg of boron
(5) from about 8 mg to about 12 mg of calcium per 10 IU of vitamin D
(6) from about 5 mg to about 10 mg of calcium per 1 mg of magnesium
(7) from about 0.9 mg to about 1.6 mg of magnesium per 10 IU of vitamin D
(8) from about 25 IU to about 50 IU of vitamin A per 10 IU of vitamin D
(9) from about 50 IU to about 100 IU of vitamin A per 1 mg of Zn
(10) from about 3 IU to about 10 IU of vitamin A per 1 IU of vitamin E
(11) from about 1.2 µg to about 1.9 µg of vitamin $B_9$ per 1 µg of vitamin $B_{12}$
(12) from about 15 IU to about 30 IU of vitamin A per 1 µg of vitamin K
(13) from about 0.1 µg to about 0.8 µg of chromium per 1 mg of vitamin C
(14) from about 3.5 mg to about 6.5 mg of vitamin $B_6$ per 1 mg of vitamin $B_9$
(15) from about 20 µg to about 60 µg of boron per 10 IU of vitamin D,
and/or in one or more ratios within the following ranges (1') to (15'):
(1') from about 7 IU to about 30 IU of vitamin E per 1 mg of zinc
(2') from about 0.8 mg to about 1.3 mg of vitamin $B_6$ per 1 mg of vitamin $B_2$
(3') from about 2.8 IU to about 3.5 IU of vitamin E per 1 µg of vitamin K
(4') from about 25 mg to about 35 mg of magnesium per 1 mg of boron
(5') from about 9 mg to about 10 mg of calcium per 10 IU of vitamin D
(6') from about 6 mg to about 9 mg of calcium per 1 mg of magnesium
(7') from about 1.0 mg to about 1.5 mg of magnesium per 10 IU of vitamin D
(8') from about 30 IU to about 45 IU of vitamin A per 10 IU of vitamin D
(9') from about 60 IU to about 90 IU of vitamin A per 1 mg of Zn
(10') from about 5 IU to about 9 IU of vitamin A per 1 IU of vitamin E
(11') from about 1.25 µg to about 1.8 µg of vitamin $B_9$ per 1 µg of vitamin $B_{12}$
(12') from about 20 IU to about 28 IU of vitamin A per 1 µg of vitamin K
(13') from about 0.2 µg to about 0.7 µg of chromium per 1 mg of vitamin C
(14') from about 4 mg to about 6 mg of vitamin $B_6$ per 1 mg of vitamin $B_9$
(15') from about 25 µg to about 55 µg of boron per 10 IU of vitamin D,
and/or in one or more ratios within the following ranges (1") to (15"):
(1") from about 8 IU to about 15 IU of vitamin E per 1 mg of zinc
(2") from about 0.9 mg to about 1.2 mg of vitamin $B_6$ per 1 mg of vitamin $B_2$
(3") from about 3.0 IU to about 3.4 IU of vitamin E per 1 µg of vitamin K
(4") from about 28 mg to about 33 mg of magnesium per 1 mg of boron
(5") from about 9.2 mg to about 9.7 mg of calcium per 10 IU of vitamin D
(6") from about 7 mg to about 8.5 mg of calcium per 1 mg of magnesium
(7") from about 1.1 mg to about 1.4 mg of magnesium per 10 IU of vitamin D
(8") from about 33 IU to about 40 IU of vitamin A per 10 IU of vitamin D
(9") from about 70 IU to about 80 IU of vitamin A per 1 mg of Zn
(10") from about 6.5 IU to about 8.5 IU of vitamin A per 1 IU of vitamin E
(11") from about 1.3 µg to about 1.7 µg of vitamin $B_9$ per 1 µg of vitamin $B_{12}$
(12") from about 24 IU to about 26 IU of vitamin A per 1 µg of vitamin K
(13") from about 0.3 µg to about 0.6 µg of chromium per 1 mg of vitamin C
(14") from about 4.5 mg to about 5.5 mg of vitamin $B_6$ per 1 mg of vitamin $B_9$
(15") from about 30 µg to about 50 µg of boron per 10 IU of vitamin D.

The present invention also provides a solid micronutrient dosage form unit which is administrable to a human. The dosage form unit comprises two or more (e.g., at least three, at least four, at least five, at least six, at least seven, at least eight or even all) micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium. The two or more micronutrients are present in the dosage form unit in at least one ratio within the following ranges (1) to (15):

(1) from about 5 IU to about 50 IU of vitamin E per 1 mg of zinc
(2) from about 0.7 mg to about 1.5 mg of vitamin $B_6$ per 1 mg of vitamin $B_2$
(3) from about 2.5 IU to about 3.6 IU of vitamin E per 1 µg of vitamin K (4) from about 20 mg to about 40 mg of magnesium per 1 mg of boron
(5) from about 8 mg to about 12 mg of calcium per 10 IU of vitamin D
(6) from about 5 mg to about 10 mg of calcium per 1 mg of magnesium
(7) from about 0.9 mg to about 1.6 mg of magnesium per 10 IU of vitamin D
(8) from about 25 IU to about 50 IU of vitamin A per 10 IU of vitamin D
(9) from about 50 IU to about 100 IU of vitamin A per 1 mg of Zn
(10) from about 3 IU to about 10 IU of vitamin A per 1 IU of vitamin E
(11) from about 1.2 µg to about 1.9 µg of vitamin $B_9$ per 1 µg of vitamin $B_{12}$
(12) from about 15 IU to about 30 IU of vitamin A per 1 µg of vitamin K
(13) from about 0.1 µg to about 0.8 µg of chromium per 1 mg of vitamin C
(14) from about 3.5 mg to about 6.5 mg of vitamin $B_6$ per 1 mg of vitamin $B_9$
(15) from about 20 µg to about 60 µg of boron per 10 IU of vitamin D, In one aspect of the dosage form unit, the two or more micronutrients may be present therein in at least one ratio within the following ranges (1') to (15'):
(1') from about 7 IU to about 30 IU of vitamin E per 1 mg of zinc
(2') from about 0.8 mg to about 1.3 mg of vitamin $B_6$ per 1 mg of vitamin $B_2$
(3') from about 2.8 IU to about 3.5 IU of vitamin E per 1 µg of vitamin K
(4') from about 25 mg to about 35 mg of magnesium per 1 mg of boron
(5') from about 9 mg to about 10 mg of calcium per 10 IU of vitamin D
(6') from about 6 mg to about 9 mg of calcium per 1 mg of magnesium
(7') from about 1.0 mg to about 1.5 mg of magnesium per 10 IU of vitamin D
(8') from about 30 IU to about 45 IU of vitamin A per 10 IU of vitamin D
(9') from about 60 IU to about 90 IU of vitamin A per 1 mg of Zn
(10') from about 5 IU to about 9 IU of vitamin A per 1 IU of vitamin E
(11') from about 1.25 µg to about 1.8 µg of vitamin $B_9$ per 1 µg of vitamin $B_{12}$
(12') from about 20 IU to about 28 IU of vitamin A per 1 µg of vitamin K
(13') from about 0.2 µg to about 0.7 µg of chromium per 1 mg of vitamin C
(14') from about 4 mg to about 6 mg of vitamin $B_6$ per 1 mg of vitamin $B_9$
(15') from about 25 µg to about 55 µg of boron per 10 IU of vitamin D
and/or in at least one ratio within the following ranges (1") to (15"):
(1") from about 8 IU to about 15 IU of vitamin E per 1 mg of zinc
(2") from about 0.9 mg to about 1.2 mg of vitamin $B_6$ per 1 mg of vitamin $B_2$
(3") from about 3.0 IU to about 3.4 IU of vitamin E per 1 µg of vitamin K
(4") from about 28 mg to about 33 mg of magnesium per 1 mg of boron
(5") from about 9.2 mg to about 9.7 mg of calcium per 10 IU of vitamin D
(6") from about 7 mg to about 8.5 mg of calcium per 1 mg of magnesium
(7") from about 1.1 mg to about 1.4 mg of magnesium per 10 IU of vitamin D
(8") from about 33 IU to about 40 IU of vitamin A per 10 IU of vitamin D
(9") from about 70 IU to about 80 IU of vitamin A per 1 mg of Zn
(10") from about 6.5 IU to about 8.5 IU of vitamin A per 1 IU of vitamin E
(11") from about 1.3 µg to about 1.7 µg of vitamin $B_9$ per 1 µg of vitamin $B_{12}$
(12") from about 24 IU to about 26 IU of vitamin A per 1 µg of vitamin K
(13") from about 0.3 µg to about 0.6 µg of chromium per 1 mg of vitamin C
(14") from about 4.5 mg to about 5.5 mg of vitamin $B_6$ per 1 mg of vitamin $B_9$
(15") from about 30 µg to about 50 µg of boron per 10 IU of vitamin D.

In another aspect, the dosage form unit may comprise at least one of these micronutrients in an amount within one of the following ranges:
(a) from about 500 IU to about 1000 IU of vitamin A
(b) from about 0.7 mg to about 1.5 mg of vitamin $B_2$
(c) from about 0.7 mg to about 2 mg of vitamin $B_6$
(d) from about 150 µg to about 300 µg of vitamin $B_9$
(e) from about 80 µg to about 250 µg of vitamin $B_{12}$
(f) from about 50 mg to about 300 mg of vitamin C
(g) from about 150 IU to about 300 IU of vitamin D
(h) from about 70 IU to about 200 IU of vitamin E
(i) from about 20 µg to about 50 µg of vitamin K
j) from about 140 mg to about 300 mg of calcium
(k) from about 15 mg to about 40 mg of magnesium
(l) from about 7 mg to about 15 mg of zinc
(m) from about 0.5 mg to about 1.5 mg of boron
(n) from about 35 µg to about 75 µg of chromium,
and/or in an amount within one of the following ranges:
(a') from about 600 to about 900 IU of vitamin A
(b') from about 0.8 mg to about 1.2 mg of vitamin $B_2$
(c') from about 0.8 mg to about 1.2 mg of vitamin $B_6$
(d') from about 180 µg to about 250 µg of vitamin $B_9$
(e') from about 100 µg to about 200 µg of vitamin $B_{12}$
(f') from about 50 mg to about 150 mg of vitamin C
(g') from about 180 IU to about 250 IU of vitamin D
(h') from about 80 IU to about 150 IU of vitamin E
(i') from about 25 µg to about 35 µg of vitamin K
(j') from about 150 mg to about 250 mg of calcium
(k') from about 20 mg to about 35 mg of magnesium
(l') from about 8 mg to about 12 mg of zinc
(m') from about 0.6 mg to about 1.1 mg of boron
(n') from about 40 µg to about 60 µg of chromium,
and/or in an amount within one of the following ranges:
(a") from about 700 to about 800 IU of vitamin A
(b") from about 0.9 mg to about 1.1 mg of vitamin $B_2$
(c") from about 0.9 mg to about 1.1 mg of vitamin $B_6$
(d") from about 190 µg to about 220 µg of vitamin $B_9$
(e") from about 140 µg to about 160 µg of vitamin $B_{12}$
(f") from about 80 mg to about 120 mg of vitamin C
(g") from about 190 IU to about 220 IU of vitamin D
(h") from about 90 IU to about 110 IU of vitamin E
(i") from about 28 µg to about 32 µg of vitamin K
(j") from about 170 mg to about 220 mg of calcium
(k") from about 25 mg to about 30 mg of magnesium
(l") from about 9 mg to about 11 mg of zinc (m″) from about 0.7 mg to about 0.9 mg of boron
(n″) from about 45 μg to about 55 μg of chromium.

In another aspect, the dosage form unit of the present invention may further comprise one of more of vitamin $B_1$, vitamin $B_3$, vitamin $B_5$, vitamin $B_7$, lycopene, lutein, zeaxanthin, copper, iodine, manganese, vanadium, molybendum, nickel, silicon and selenium. For example, it may comprise at least one of these micronutrients in amount within one of the following ranges:

(o) from about 3 mg to about 8 mg of vitamin $B_3$
(p) from about 0.5 mg to about 5 mg of lutein
(q) from about 1 mg to about 8 mg of zeaxanthin
(r) from about 25 μg to about 60 μg of nickel
(s) from about 0.5 mg to about 5 mg of silicon
(t) from about 20 μg to about 100 μg of selenium
(u) from about 0.2 mg to about 1.2 mg of vitamin $B_1$
(v) from about 0.5 mg to about 4 mg of vitamin $B_5$
(w) from about 5 μg to about 50 μg of vitamin $B_7$
(x) from about 0.5 mg to about 4 mg of lycopene
(y) from about 10 μg to about 50 μg of iodine
(z) from about 0.2 mg to about 1 mg of manganese
(aa) from about 1 μg to about 8 μg of vanadium
(bb) from about 7 μg to about 40 μg of molybdenum
(cc) from about 0.3 mg to about 2 mg of copper, and/or in an amount within one of the following ranges:
(o') from about 4 mg to about 7 mg of vitamin $B_3$
(p') from about 1 mg to about 2.5 mg of lutein
(q') from about 1.5 mg to about 4 mg of zeaxanthin
(r') from about 30 μg to about 50 μg of nickel
(s') from about 1 mg to about 3 mg of silicon
(t') from about 30 μg to about 70 μg of selenium
(u') from about 0.3 mg to about 0.8 mg of vitamin $B_1$
(v') from about 1.5 mg to about 2.5 mg of vitamin $B_5$
(w') from about 10 μg to about 30 μg of vitamin $B_7$
(x') from about 1 mg to about 2 mg of lycopene
(y') from about 20 μg to about 40 μg of iodine
(z') from about 0.3 mg to about 0.7 mg of manganese
(aa') from about 1.5 μg to about 4 μg of vanadium
(bb') from about 10 μg to about 25 μg of molybdenum
(cc') from about 0.5 mg to about 1 mg of copper, and/or in an amount within one of the following ranges:
(o″) from about 4.5 mg to about 5.5 mg of vitamin $B_3$
(p″) from about 1.2 mg to about 1.8 mg of lutein
(q″) from about 2 mg to about 3 mg of zeaxanthin
(r″) from about 35 μg to about 45 μg of nickel
(s″) from about 1.5 mg to about 2 mg of silicon
(t″) from about 40 μg to about 60 μg of selenium
(u″) from about 0.4 mg to about 0.6 mg of vitamin $B_1$
(v″) from about 1.7 mg to about 2.2 mg of vitamin $B_5$
(w″) from about 15 μg to about 25 μg of vitamin $B_7$
(x″) from about 1.3 mg to about 1.7 mg of lycopene
(y″) from about 25 μg to about 35 tμg of iodine
(z″) from about 0.4 mg to about 0.6 mg of manganese
(aa″) from about 2 μg to about 3 μg of vanadium
(bb″) from about 12 μg to about 18 μg of molybdenum
(cc″) from about 0.6 mg to about 0.8 mg of copper.

In another aspect, the dosage form unit of the present invention may comprise at least 15 micronutrients selected from vitamin $B_2$, vitamin $B_3$, vitamin $B_6$, vitamin $B_9$, vitamin $B_{12}$, vitamin D, vitamin K, lutein, zeaxanthin, calcium, magnesium, chromium, nickel, zinc, boron, silicon and selenium.

In yet another aspect, the dosage form unit of the present invention may be in the form of a tablet, a capsule or a caplet.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

As set forth above, the present invention provides, inter alia, 24-hour micronutrient dosage units which comprise certain micronutrients in certain ratios and, optionally, certain amounts. In this regard, it is to be appreciated that a dosage unit is not the same as a dosage form unit such as, e.g., a tablet, a capsule, a caplet, a pill, a lozenge or a chewable tablet (as also provided by the present invention). In other words, a dosage unit of the present invention merely indicates the ratios and optionally the amounts of micronutrients which are to be ingested by a human over a period of about 24 hours and does not require the micronutrients to be present in a single dosage form unit (although this is possible).

Merely by way of example, a dosage unit according to the present invention may by present in a single dosage form unit (e.g., a single tablet or a single capsule) or in two, three, four or more dosage form units (e.g., two, three, four or more tablets or two, three, four or more capsules). If two or more dosage form units are present, these units may be identical or different and preferably are identical.

If a dosage unit of the present invention is constituted by, e.g., two dosage form units, these units may be identical, i.e., each of them may comprise all of the micronutrients which are to be provided by the dosage unit in the same ratios and the same amounts. However, it is also possible for these two dosage form units to be different in several respects. For example, (i) one of the dosage form units may be, e.g., a tablet and the other one may be different from a tablet (e.g., may be a capsule) and/or (ii) one of the dosage form units may comprise one or more of the micronutrients which are to be provided by the dosage unit of the present invention and the other one may comprise the remainder of these micronutrients and/or (iii) a first dosage form unit may comprise all of the micronutrients which are to be provided by the dosage unit of the present invention and a second dosage form unit may also comprise all of these micronutrients, but in amounts and/or ratios which are different from those in the first dosage form unit. All that matters here is that these two dosage form units together provide the intended (24-hour) dosage unit. Accordingly, the two dosage form units may be ingested by the human at about the same time or separated by an interval of, e.g., one or more hours. For example, one of them may be for ingestion in the morning and the other one may be for ingestion in the evening.

Providing a dosage unit of the present invention in the form of two or more different dosage form units may be advantageous, for example, if different formulations of different micronutrients are desirable in order to optimize the bioavailability of the micronutrients and/or if one micronutrient interferes with the bioavailability of another micronutrient and/or if a administration of certain micronutrients at different times (of the day) may be of advantage. In this regard, it is noted that in certain scenarios an alternative to providing different dosage form units may be the provision of a multilayered (e.g., bilayered) tablet. In this case the advantages of physically separating micronutrients which may interfere with each other when present in the same (single) formulation and of being able to release different micronutrients at different times and/or with different rates can be combined.

Of course, the above explanations apply correspondingly if three, four or more dosage form units together constitute a 24-hour dosage unit according to the present invention. In a preferred embodiment, two to four (preferably identical) dosage form units constitute a 24-hour dosage unit of the present invention.

The dosage form units of the present invention are preferably solid, but semi-liquid or liquid dosage form units (such as, e.g., gels, syrups, suspensions, etc.) may be used as well. For example, it would also be possible to have a solid dosage form such as, e.g., a soft or hard gelatine capsule which is filled with a liquid formulation.

A 24-hour dosage unit of the present invention comprises at least two and preferably more than two (e.g., at least three, at least four, at least five, at least six or at least seven) micronutrients in ratios which are within certain ranges. In this regard, it is to be appreciated that even if more than two micronutrients selected from vitamin A, vitamin $B_2$, vitamin $B_6$, vitamin $B_9$, vitamin $B_{12}$, vitamin C, vitamin D, vitamin E, vitamin K, calcium, magnesium, zinc, boron and chromium are present according to the present invention it is sufficient if two of them are present in a ratio according to the present invention although it is, of course, preferred that all or at least almost all of the micronutrients are present in ratios which are within the indicated ranges.

According to the present invention, if vitamin E and zinc are to be comprised in a dosage unit of the present invention the amount of vitamin E which is present per 1 mg of zinc is usually not lower than about 5 IU (International Units), e.g., not lower than about 8 IU or not lower than about 9 IU, but is usually not higher than about 50 IU, e.g., not higher than about 40 IU, not higher than about 30 IU, not higher than about 20 IU, not higher than about 15 IU, or not higher than about 12 IU. Of course, if a dosage unit comprises two or more (e.g., three or four) identical dosage form unit the same applies to the individual dosage form units (e.g., tablets, capsules, caplets, pills, lozenges, etc.).

Natural vitamin E exists in eight different forms, four tocopherols and four tocotrienols. Both the tocopherols and tocotrienols occur in alpha, beta, gamma and delta forms. Each form has slightly different biological activity and each form and each mixture of two or more thereof can be employed in the dosage unit of the present invention. 1 IU of vitamin E is defined as the biological equivalent of 0.667 milligrams of RRR-alpha-tocopherol or of 1 milligram of all-rac-alpha-tocopheryl acetate (commercially called dl-alpha-tocopheryl acetate). A preferred form of vitamin E for the purposes of the present invention comprises d-alpha-tocopheryl acetate.

If vitamin $B_6$ (also known as pyridoxine, e.g., in the form of pyridoxine hydrochloride) and vitamin $B_2$ (also known as riboflavin) are to be comprised in a dosage unit of the present invention the amount of vitamin $B_6$ which is present per 1 mg of vitamin $B_2$ is usually not lower than about 0.7 mg, e.g., not lower than about 0.8 mg or not lower than about 1.0 mg, but is usually not higher than about 1.5 mg, e.g., not higher than about 1.3 mg, or not higher than about 1.2 mg.

If vitamin E and vitamin K are to be comprised in a dosage unit of the present invention the amount of vitamin E which is present per 1 mg of vitamin K is usually not lower than about 2.5 IU, e.g., not lower than about 2.8 IU or not lower than about 3.0 IU, but is usually not higher than about 3.6 IU, e.g., not higher than about 3.5 IU, or not higher than about 3.4 IU.

If magnesium and boron are to be comprised in a dosage unit of the present invention the amount of magnesium which is present per 1 mg of boron is usually not lower than about 20 mg, e.g., not lower than about 25 mg or not lower than about 28 mg, but is usually not higher than about 40 mg, e.g., not higher than about 35 mg, or not higher than about 33 mg.

If calcium and vitamin D are to be comprised in a dosage unit of the present invention, the amount of calcium which is present per 10 IU of vitamin D is usually not lower than about 8 mg, e.g., not lower than about 9 mg or not lower than about 9.2 mg, but is usually not higher than about 12 mg, e.g., not higher than about 11 mg, not higher than about 10 mg, or not higher than about 9.7 mg.

Vitamin D is the generic name of a group of fat-soluble prohormones, the two major forms of which are vitamin $D_2$ (or ergocalciferol) and vitamin $D_3$ (or cholecalciferol). Other forms of vitamin D include vitamin $D_1$, vitamin $D_4$ and vitamin $D_5$. The term vitamin D also refers to metabolites and other analogues of these substances. Vitamin $D_3$ is produced in skin exposed to sunlight, specifically ultraviolet B radiation. One microgram (μg) of any of the above substances corresponds to 40 IU of vitamin E. One preferred form of vitamin D for the purposes of the present invention is cholecalciferol.

If calcium and magnesium are to be comprised in a dosage unit of the present invention the amount of calcium which is present per 1 mg of magnesium is usually not lower than about 5 mg, e.g., not lower than about 6 mg or not lower than about 7 mg, but is usually not higher than about 10 mg, e.g., not higher than about 9 mg, or not higher than about 8.5 mg.

If magnesium and vitamin D are to be comprised in a dosage unit of the present invention the amount of magnesium which is present per 10 IU of vitamin D is usually not lower than about 0.9 mg, e.g., not lower than about 1.0 mg or not lower than about 1.1 mg, but is usually not higher than about 1.6 mg, e.g., not higher than about 1.5 mg, or not higher than about 1.4 mg.

If vitamin A and vitamin D are to be comprised in a dosage unit of the present invention the amount of vitamin A which is present per 10 IU of vitamin D is usually not lower than about 25 IU, e.g., not lower than about 30 IU or not lower than about 33 IU, but is usually not higher than about 50 IU, e.g., not higher than about 45 IU, or not higher than about 40 IU.

Vitamin A exists not as a single compound, but in several forms. In foods of animal origin the major form of vitamin A is retinol, but vitamin A can also exist as retinal and/or as retinoic acid. Precursors to the vitamin are present in foods of plant origin as some of the members of the carotenoid family of compounds. Vitamin A intake is expressed in IU, with 1 IU=0.3 micrograms (μg) of retinol. For other compounds of the vitamin A family a higher amount (in micrograms) is required for 1 IU of vitamin A. For example, 0.6 micrograms of beta-carotene are required for 1 IU of vitamin A. According to the present invention, vitamin A is preferably provided as retinol, either alone or in combination with one or more other members of the carotenoid family. Often, at least about 30%, e.g., at least about 40%, or at least about 50% by weight of vitamin A will be provided in the form of retinol. For example, vitamin A may be provided in combination with beta-carotene, e.g., in a weight ratio of from about 7:3 to about 3:7 or from about 6:4 to about 4:6. One preferred form of vitamin A for the purposes of the present invention is beta-carotene in combination with retinol palmitate.

If vitamin A and zinc are to be comprised in a dosage unit of the present invention the amount of vitamin A which is present per 1 mg of zinc is usually not lower than about 50 IU, e.g., not lower than about 60 IU or not lower than about 70 IU, but is usually not higher than about 100 IU, e.g., not higher than about 90 IU, or not higher than about 80 IU.

If vitamin A and vitamin E are to be comprised in a dosage unit of the present invention the amount of vitamin A which is present per 1 IU of vitamin E is usually not lower than about 3 IU, e.g., not lower than about 5 IU or not lower than about 6.5 IU, but is usually not higher than about 10 IU, e.g., not higher than about 9 IU, or not higher than about 8.5 IU.

If vitamin $B_9$ (also known as folic acid) and vitamin $B_{12}$ (also known as cobalamin) are to be comprised in a dosage unit of the present invention the amount of vitamin $B_9$ which is present per 1 mg of vitamin $B_{12}$ is usually not lower than about 1.1 µg, e.g., not lower than about 1.2 µg, not lower than about 1.25 µg or not lower than about 1.3 µg, but is usually not higher than about 1.9 µg, e.g., not higher than about 1.8 µg, or not higher than about 1.7 µg.

The active form of folic acid in the human body is known to be L-methylfolate which can completely or partially replace the folic acid in the dosage (form) unit of the present invention and is used in approximately the same amounts and ratios as folic acid, although the amount of L-methylfolate may optionally be up to about 25% less than a corresponding amount of folic acid.

In this regard, it is to be appreciated that whenever a (any) non-mineral micronutrient (e.g., a vitamin) is mentioned in the present specification and the appended claims the mentioning of the non-mineral micronutrient is intended to encompass not only the presence of the non-mineral micronutrient itself but also the presence of any precursors (e.g., compounds which are converted by the body to form the non-mineral micronutrient) and metabolites (e.g., compounds into which the body will break down or convert the non-mineral micronutrient and which are structurally related to the non-mineral micronutrient) thereof. For example, if it is mentioned herein that a particular non-mineral micronutrient is to be present in a certain amount this also covers situations where an equivalent amount (e.g., an about equivalent molar amount and/or an amount which has approximately the same effect as the specified amount of the stated amount of the non-mineral micronutrient) of a precursor and/or a metabolite of this non-mineral micronutrient is present. Of course, it also covers situations where the non-mineral micronutrient and the precursor and/or the metabolite are present at the same time.

If vitamin A and vitamin K are to be comprised in a dosage unit of the present invention the amount of vitamin A which is present per 1 µg of vitamin K is usually not lower than about 15 IU, e.g., not lower than about 20 IU or not lower than about 24 IU, but is usually not higher than about 30 IU, e.g., not higher than about 28 IU, or not higher than about 26 IU.

If chromium and vitamin C are to be comprised in a dosage unit of the present invention the amount of chromium which is present per 1 mg of vitamin C is usually not lower than about 0.1 µg, e.g., not lower than about 0.2 µg or not lower than about 0.3 µg, but is usually not higher than about 0.8 µg, e.g., not higher than about 0.7 µg, or not higher than about 0.6 µg.

If vitamin $B_6$ and vitamin $B_9$ are to be comprised in a dosage unit of the present invention the amount of vitamin $B_6$ which is present per 1 mg of vitamin $B_9$ is usually not lower than about 3.5 mg, e.g., not lower than about 4 mg or not lower than about 4.5 mg, but is usually not higher than about 6.5 mg, e.g., not higher than about 6 mg, or not higher than about 5.5 mg.

If boron and vitamin D are to be comprised in a dosage unit of the present invention, the amount of boron which is present per 10 IU of vitamin D is usually not lower than about 20 µg, e.g., not lower than about 25 µg or not lower than about 30 µg, but is usually not higher than about 60 µg, e.g., not higher than about 55 µg, or not higher than about 50 µg.

If vitamin A is to be comprised in a 24-hour dosage unit of the present invention, it is employed in an amount which is usually not lower than about 1000 IU, e.g., not lower than about 1500 IU or not lower than about 1800 IU, but is usually not higher than about 3500 IU, e.g., not higher than about 3200 IU or not higher than about 3000 IU. These amounts also apply if a single 24-hour dosage form unit which comprises vitamin A is to be provided. If four dosage form units with identical amounts of vitamin A are to be provided to make up a 24-hour dosage unit, vitamin A is present in each of these dosage form units in an amount which is usually not lower than about 500 IU, e.g., not lower than about 600 IU or not lower than about 700 IU, but is usually not higher than about 1000 IU, e.g., not higher than about 900 IU or not higher than about 800 IU.

If vitamin $B_2$ (riboflavin) is to be comprised in a 24-hour dosage unit of the present invention, it is employed in an amount which is usually not lower than about 2 mg, e.g., not lower than about 2.5 mg or not lower than about 3 mg, but is usually not higher than about 5.5 mg, e.g., not higher than about 5 mg or not higher than about 4.5 mg. These amounts also apply if a single 24-hour dosage form unit which comprises vitamin $B_2$ is to be provided. If four dosage form units with identical amounts of vitamin $B_2$ are to be provided to make up a 24-hour dosage unit, vitamin $B_2$ is present in each of these dosage form units in an amount which is usually not lower than about 0.7 mg, e.g., not lower than about 0.8 mg or not lower than about 0.9 mg, but is usually not higher than about 1.5 mg, e.g., not higher than about 1.2 mg or not higher than about 1.1 mg.

If vitamin $B_6$ (pyridoxine, e.g., in the form of pyridoxine hydrochloride) is to be comprised in a 24-hour dosage unit of the present invention, it is employed in an amount which is usually not lower than about 2.5 mg, e.g., not lower than about 3 mg or not lower than about 3.5 mg, but is usually not higher than about 6 mg, e.g., not higher than about 5 mg or not higher than about 4.5 mg. These amounts also apply if a single 24-hour dosage form unit which comprises vitamin $B_6$ is to be provided. If four dosage form units with identical amounts of vitamin $B_6$ are to be provided to make up a 24-hour dosage unit, vitamin $B_6$ is present in each of these dosage form units in an amount which is usually not lower than about 0.7 mg, e.g., not lower than about 0.8 mg or not lower than about 0.9 mg, but is usually not higher than about 2 mg, e.g., not higher than about 1.2 mg or not higher than about 1.1 mg.

If vitamin $B_9$ (folic acid) is to be comprised in a 24-hour dosage unit of the present invention, it is employed in an amount which is usually not lower than about 400 µg, e.g., not lower than about 600 µg or not lower than about 700 µg, but is usually not higher than about 1 mg, e.g., not higher than about 900 µg or not higher than about 850 µg. These amounts also apply if a single 24-hour dosage form unit which comprises vitamin $B_9$ is to be provided. If four dosage form units with identical amounts of vitamin $B_9$ are to be provided to make up a 24-hour dosage unit, vitamin $B_9$ is present in each of these dosage form units in an amount which is usually not lower than about 150 µg, e.g., not lower than about 180 µg or not lower than about 190 µg, but is usually not higher than about 300 µg, e.g., not higher than about 250 µg or not higher than about 220 µg.

If vitamin $B_{12}$ (e.g., cyanocobalamin) is to be comprised in a 24-hour dosage unit of the present invention, it is employed in an amount which is usually not lower than about 250 µg, e.g., not lower than about 350 µg or not lower than about 500 µg, but is usually not higher than about 750 µg, e.g., not higher than about 700 µg or not higher than about 650 µg. These amounts also apply if a single 24-hour dosage form unit which comprises vitamin $B_{12}$ is to be provided. If four dosage form units with identical amounts of vitamin $B_{12}$ are to be provided to make up a 24-hour dosage unit, vitamin $B_{12}$ is present in each of these dosage form units in an amount which is usually not lower than about 80 μg, e.g., not lower than about 100 μg or not lower than about 140 μg, but is usually not higher than about 250 μg, e.g., not higher than about 200 μg or not higher than about 160 μg.

If vitamin C (ascorbic acid) is to be comprised in a 24-hour dosage unit of the present invention, it is employed in an amount which is usually not lower than about 200 mg, e.g., not lower than about 300 mg or not lower than about 350 mg, but is usually not higher than about 2000 mg, e.g., not higher than about 1800 mg or not higher than about 1600 mg. These amounts also apply if a single 24-hour dosage form unit which comprises vitamin C is to be provided. If four dosage form units with identical amounts of vitamin C are to be provided to make up a 24-hour dosage unit, vitamin C is present in each of these dosage form units in an amount which is usually not lower than about 50 mg, e.g., not lower than about 70 mg or not lower than about 80 mg, but is usually not higher than about 300 mg, e.g., not higher than about 150 mg or not higher than about 120 mg.

If vitamin D is to be comprised in a 24-hour dosage unit of the present invention, it is employed in an amount which is usually not lower than about 300 IU, e.g., not lower than about 400 IU or not lower than about 500 IU, but is usually not higher than about 1000 IU, e.g., not higher than about 900 IU or not higher than about 850 IU. These amounts also apply if a single 24-hour dosage form unit which comprises vitamin D is to be provided. If four dosage form units with identical amounts of vitamin D are to be provided to make up a 24-hour dosage unit, vitamin D is present in each of these dosage form units in an amount which is usually not lower than about 150 IU, e.g., not lower than about 180 IU or not lower than about 190 IU, but is usually not higher than about 300 IU, e.g., not higher than about 250 IU or not higher than about 220 IU.

If vitamin E (e.g., in the form of d-alpha tocopherol succinate) is to be comprised in a 24-hour dosage unit of the present invention, it is employed in an amount which is usually not lower than about 200 IU, e.g., not lower than about 300 IU or not lower than about 350 IU, but is usually not higher than about 700 IU, e.g., not higher than about 600 IU or not higher than about 500 IU. These amounts also apply if a single 24-hour dosage form unit which comprises vitamin E is to be provided. If four dosage form units with identical amounts of vitamin E are to be provided to make up a 24-hour dosage unit, vitamin E is present in each of these dosage form units in an amount which is usually not lower than about 70 IU, e.g., not lower than about 80 IU or not lower than about 90 IU, but is usually not higher than about 200 IU, e.g., not higher than about 150 IU or not higher than about 110 IU.

If vitamin K is to be comprised in a 24-hour dosage unit of the present invention, it is employed in an amount which is usually not lower than about 80 μg, e.g., not lower than about 100 μg or not lower than about 110 μg, but is usually not higher than about 200 μg, e.g., not higher than about 170 μg or not higher than about 150 μg. These amounts also apply if a single 24-hour dosage form unit which comprises vitamin K is to be provided. If four dosage form units with identical amounts of vitamin K are to be provided to make up a 24-hour dosage unit, vitamin K is present in each of these dosage form units in an amount which is usually not lower than about 20 μg, e.g., not lower than about 25 μg or not lower than about 28 μg, but is usually not higher than about 50 μg, e.g., not higher than about 35 μg or not higher than about 32 μg.

If vitamin $B_3$ (niacin, includes nicotinic acid and nicotinamide) is to be comprised in a 24-hour dosage unit of the present invention, it is employed in an amount which is usually not lower than about 4 mg, e.g., not lower than about 15 mg or not lower than about 18 mg, but is usually not higher than about 35 mg, e.g., not higher than about 25 mg or not higher than about 22 mg. These amounts also apply if a single 24-hour dosage form unit which comprises vitamin $B_3$ is to be provided. If four dosage form units with identical amounts of vitamin $B_3$ are to be provided to make up a 24-hour dosage unit, vitamin $B_3$ is present in each of these dosage form units in an amount which is usually not lower than about 3 mg, e.g., not lower than about 4 mg or not lower than about 4.5 mg, but is usually not higher than about 8 mg, e.g., not higher than about 7 mg or not higher than about 5.5 mg.

If vitamin $B_1$ (thiamine, e.g., in the form of thiamine monocitrate or thiamine hydrochloride) is to be comprised in a 24-hour dosage unit of the present invention, it is employed in an amount which is usually not lower than about 0.5 mg, e.g., not lower than about 1 mg or not lower than about 1.5 mg, but is usually not higher than about 5 mg, e.g., not higher than about 3 mg or not higher than about 2.5 mg. These amounts also apply if a single 24-hour dosage form unit which comprises vitamin $B_1$ is to be provided. If four dosage form units with identical amounts of vitamin $B_1$ are to be provided to make up a 24-hour dosage unit, vitamin $B_1$ is present in each of these dosage form units in an amount which is usually not lower than about 0.2 mg, e.g., not lower than about 0.3 mg or not lower than about 0.4 mg, but is usually not higher than about 1.2 mg, e.g., not higher than about 0.8 mg or not higher than about 0.6 mg.

If vitamin $B_5$ (pantothenic acid, e.g., in the form of (d-) calcium pantothenate) is to be comprised in a 24-hour dosage unit of the present invention, it is employed in an amount which is usually not lower than about 1 mg, e.g., not lower than about 3 mg or not lower than about 4 mg, but is usually not higher than about 25 mg, e.g., not higher than about 15 mg or not higher than about 10 mg. These amounts also apply if a single 24-hour dosage form unit which comprises vitamin $B_5$ is to be provided. If four dosage form units with identical amounts of vitamin $B_5$ are to be provided to make up a 24-hour dosage unit, vitamin $B_5$ is present in each of these dosage form units in an amount which is usually not lower than about 0.5 mg, e.g., not lower than about 1.5 mg or not lower than about 1.7 mg, but is usually not higher than about 4 mg, e.g., not higher than about 2.5 mg or not higher than about 2.2 mg.

If vitamin $B_7$ (also known as vitamin H or biotin, e.g., in the form of d-biotin) is to be comprised in a 24-hour dosage unit of the present invention, it is employed in an amount which is usually not lower than about 10 μg, e.g., not lower than about 25 μg or not lower than about 40 μg, but is usually not higher than about 0.1 mg, e.g., not higher than about 0.09 mg or not higher than about 85 μg. These amounts also apply if a single 24-hour dosage form unit which comprises vitamin $B_7$ is to be provided. If four dosage form units with identical amounts of vitamin $B_7$ are to be provided to make up a 24-hour dosage unit, vitamin $B_7$ is present in each of these dosage form units in an amount which is usually not lower than about 5 μg, e.g., not lower than about 10 μg or not lower than about 15 μg, but is usually not higher than about 0.05 mg, e.g., not higher than about 30 μg or not higher than about 25 μg.

If lutein is to be comprised in a 24-hour dosage unit of the present invention, it is employed in an amount which is usually not lower than about 2 mg, e.g., not lower than about 3 mg or not lower than about 5 mg, but is usually not higher than about 20 mg, e.g., not higher than about 15 mg or not higher than about 8 mg. These amounts also apply if a single 24-hour dosage form unit which comprises lutein is to be provided. If four dosage form units with identical amounts of lutein are to be provided to make up a 24-hour dosage unit, lutein is present in each of these dosage form units in an amount which is usually not lower than about 0.5 mg, e.g., not lower than about 1 mg or not lower than about 1.2 mg, but is usually not higher than about 5 mg, e.g., not higher than about 2.5 mg or not higher than about 1.8 mg.

If zeaxanthin is to be comprised in a 24-hour dosage unit of the present invention, it is employed in an amount which is usually not lower than about 2 mg, e.g., not lower than about 5 mg or not lower than about 8 mg, but is usually not higher than about 25 mg, e.g., not higher than about 20 mg or not higher than about 15 mg. These amounts also apply if a single 24-hour dosage form unit which comprises zeaxanthin is to be provided. If four dosage form units with identical amounts of zeaxanthin are to be provided to make up a 24-hour dosage unit, zeaxanthin is present in each of these dosage form units in an amount which is usually not lower than about 1 mg, e.g., not lower than about 1.5 mg or not lower than about 2 mg, but is usually not higher than about 8 mg, e.g., not higher than about 4 mg or not higher than about 3 mg. Zeaxanthin may be replaced completely or partially by equivalent amounts of mesozeaxanthin.

If lycopene is to be comprised in a 24-hour dosage unit of the present invention, it is employed in an amount which is usually not lower than about 2 mg, e.g., not lower than about 3 mg or not lower than about 4 mg, but is usually not higher than about 25 mg, e.g., not higher than about 15 mg or not higher than about 10 mg. These amounts also apply if a single 24-hour dosage form unit which comprises lycopene is to be provided. If four dosage form units with identical amounts of lycopene are to be provided to make up a 24-hour dosage unit, lycopene is present in each of these dosage form units in an amount which is usually not lower than about 0.5 mg, e.g., not lower than about 1 mg or not lower than about 1.3 mg, but is usually not higher than about 4 mg, e.g., not higher than about 2 mg or not higher than about 1.7 mg.

If calcium is to be comprised in a 24-hour dosage unit of the present invention, it is employed in an amount which is usually not lower than about 600 mg, e.g., not lower than about 650 mg or not lower than about 700 mg, but is usually not higher than about 900 mg, e.g., not higher than about 850 mg or not higher than about 800 mg. These amounts also apply if a single 24-hour dosage form unit which comprises calcium is to be provided. If four dosage form units with identical amounts of calcium are to be provided to make up a 24-hour dosage unit, calcium is present in each of these dosage form units in an amount which is usually not lower than about 140 mg, e.g., not lower than about 150 mg or not lower than about 170 mg, but is usually not higher than about 300 mg, e.g., not higher than about 250 mg or not higher than about 220 mg. Calcium can be provided in any pharmaceutically acceptable form such as, e.g., one or more of calcium pantothenate, dicalcium phosphate, calcium carbonate, calcium silicate, calcium citrate, calcium bisglycinate or any other calcium amino acid salt or amino acid chelate. One preferred source of calcium for the purposes of the present invention is calcium carbonate.

If magnesium is to be comprised in a 24-hour dosage unit of the present invention, it is employed in an amount which is usually not lower than about 50 mg, e.g., not lower than about 70 mg or not lower than about 80 mg, but is usually not higher than about 150 mg, e.g., not higher than about 130 mg or not higher than about 120 mg. These amounts also apply if a single 24-hour dosage form unit which comprises magnesium is to be provided. If four dosage form units with identical amounts of magnesium are to be provided to make up a 24-hour dosage unit, magnesium is present in each of these dosage form units in an amount which is usually not lower than about 15 mg, e.g., not lower than about 20 mg or not lower than about 25 mg, but is usually not higher than about 40 mg, e.g., not higher than about 35 mg or not higher than about 30 mg. Magnesium can be provided in any pharmaceutically acceptable form such as, e.g., one or more of magnesium gluconate, magnesium aspartate, magnesium citrate, magnesium stearate, magnesium carbonate, magnesium oxide, magnesium hydroxide, magnesium sulfate and a magnesium amino acid chelate. One preferred source of magnesium for the purposes of the present invention is magnesium oxide.

If zinc is to be comprised in a 24-hour dosage unit of the present invention, it is employed in an amount which is usually not lower than about 10 mg, e.g., not lower than about 20 mg or not lower than about 25 mg, but is usually not higher than about 60 mg, e.g., not higher than about 50 mg or not higher than about 45 mg. These amounts also apply if a single 24-hour dosage form unit which comprises zinc is to be provided. If four dosage form units with identical amounts of zinc are to be provided to make up a 24-hour dosage unit, zinc is present in each of these dosage form units in an amount which is usually not lower than about 7 mg, e.g., not lower than about 8 mg or not lower than about 9 mg, but is usually not higher than about 15 mg, e.g., not higher than about 12 mg or not higher than about 11 mg. Zinc can be provided in any pharmaceutically acceptable form such as, e.g., one or more of zinc sulfate (heptahydrate), zinc chloride, zinc oxide, zinc aspartate, zinc gluconate, zinc monomethionate or any other amino acid salt or amino acid chelate of zinc. One preferred source of zinc for the purposes of the present invention is zinc oxide, preferably at least partly in delayed release form.

If boron is to be comprised in a 24-hour dosage unit of the present invention, it is employed in an amount which is usually not lower than about 2 mg, e.g., not lower than about 2.5 mg or not lower than about 2.8 mg, but is usually not higher than about 6 mg, e.g., not higher than about 4.5 mg or not higher than about 4 mg. These amounts also apply if a single 24-hour dosage form unit which comprises boron is to be provided. If four dosage form units with identical amounts of boron are to be provided to make up a 24-hour dosage unit, boron is present in each of these dosage form units in an amount which is usually not lower than about 0.5 mg, e.g., not lower than about 0.6 mg or not lower than about 0.7 mg, but is usually not higher than about 1.5 mg, e.g., not higher than about 1.1 mg or not higher than about 0.9 mg. Boron can be provided in any pharmaceutically acceptable form such as, e.g., as boron citrate and/or an aminoate. One preferred source of boron for the purposes of the present invention is a boron amino acid chelate.

If chromium is to be comprised in a 24-hour dosage unit of the present invention, it is employed in an amount which is usually not lower than about 100 µg, e.g., not lower than about 120 µg or not lower than about 150 µg, but is usually not higher than about 300 µg, e.g., not higher than about 270 µg or not higher than about 250 µg. These amounts also apply if a single 24-hour dosage form unit which comprises chromium is to be provided. If four dosage form units with identical amounts of chromium are to be provided to make up a 24-hour dosage unit, chromium is present in each of these dosage form units in an amount which is usually not lower than about 35 Rig, e.g., not lower than about 40 µg or not lower than about 45 µg, but is usually not higher than about 75 µg, e.g., not higher than about 60 µg or not higher than about 55 μg. Chromium can be provided in any pharmaceutically acceptable form such as, e.g., one or more of chromium chloride, chromium picolinate, chromium polynicotinate, yeast-bound chromium, GTF chromium, niacin-bound chromium and amino acid chelates of chromium. One preferred source of chromium for the purposes of the present invention is a chromium amino acid chelate.

If nickel is to be comprised in a 24-hour dosage unit of the present invention, it is employed in an amount which is usually not lower than about 5 μg, e.g., not lower than about 100 μg or not lower than about 130 μg, but is usually not higher than about 300 μg, e.g., not higher than about 200 μg or not higher than about 170 μg. These amounts also apply if a single 24-hour dosage form unit which comprises nickel is to be provided. If four dosage form units with identical amounts of nickel are to be provided to make up a 24-hour dosage unit, nickel is present in each of these dosage form units in an amount which is usually not lower than about 25 μg, e.g., not lower than about 30 μg or not lower than about 35 μg, but is usually not higher than about 60 μg, e.g., not higher than about 50 μg or not higher than about 45 Lg. Nickel can be provided in any pharmaceutically acceptable form such as, e.g., an amino acid salt or chelate. One preferred source of nickel for the purposes of the present invention is a nickel amino acid chelate.

If silicon is to be comprised in a 24-hour dosage unit of the present invention, it is employed in an amount which is usually not lower than about 2 mg, e.g., not lower than about 3 mg or not lower than about 4 mg, but is usually not higher than about 25 mg, e.g., not higher than about 15 mg or not higher than about 10 mg. These amounts also apply if a single 24-hour dosage form unit which comprises silicon is to be provided. If four dosage form units with identical amounts of silicon are to be provided to make up a 24-hour dosage unit, silicon is present in each of these dosage form units in an amount which is usually not lower than about 0.5 mg, e.g., not lower than about 1 mg or not lower than about 1.5 mg, but is usually not higher than about 5 mg, e.g., not higher than about 3 mg or not higher than about 2 mg. Silicon can be provided in any pharmaceutically acceptable form such as, e.g., one or more of silicon dioxide and calcium silicate.

If selenium is to be comprised in a 24-hour dosage unit of the present invention, it is employed in an amount which is usually not lower than about 25 μg, e.g., not lower than about 50 μg or not lower than about 150 μg, but is usually not higher than about 300 μg, e.g., not higher than about 250 μg or not higher than about 220 Lg. These amounts also apply if a single 24-hour dosage form unit which comprises selenium is to be provided. If four dosage form units with identical amounts of selenium are to be provided to make up a 24-hour dosage unit, selenium is present in each of these dosage form units in an amount which is usually not lower than about 20 μg, e.g., not lower than about 30 μg or not lower than about 40 μg, but is usually not higher than about 100 μg, e.g., not higher than about 70 μg or not higher than about 60 μg. Selenium can be provided in any pharmaceutically acceptable form such as, e.g., one or more of sodium selenate, selenium monomethionine and other selenium aminoates. One preferred source of selenium for the purposes of the present invention is sodium selenite.

If iodine is to be comprised in a 24-hour dosage unit of the present invention, it is employed in an amount which is usually not lower than about 30 μg, e.g., not lower than about 50 μg or not lower than about 70 μg, but is usually not higher than about 0.2 mg, e.g., not higher than about 150 μg or not higher than about 130 μg. These amounts also apply if a single 24-hour dosage form unit which comprises iodine is to be provided. If four dosage form units with identical amounts of iodine are to be provided to make up a 24-hour dosage unit, iodine is present in each of these dosage form units in an amount which is usually not lower than about 10 μg, e.g., not lower than about 20 μg or not lower than about 25 μg, but is usually not higher than about 0.05 mg, e.g., not higher than about 40 μg or not higher than about 35 μg. Iodine can be provided in any pharmaceutically acceptable form such as, e.g., one or more of potassium iodide, sodium iodide and kelp. One preferred source of iodine for the purposes of the present invention is potassium iodide.

If manganese is to be comprised in a 24-hour dosage unit of the present invention, it is employed in an amount which is usually not lower than about 1 mg, e.g., not lower than about 1.5 mg or not lower than about 1.8 mg, but is usually not higher than about 4 mg, e.g., not higher than about 3 mg or not higher than about 2.5 mg. These amounts also apply if a single 24-hour dosage form unit which comprises manganese is to be provided. If four dosage form units with identical amounts of manganese are to be provided to make up a 24-hour dosage unit, manganese is present in each of these dosage form units in an amount which is usually not lower than about 0.2 mg, e.g., not lower than about 0.3 mg or not lower than about 0.4 mg, but is usually not higher than about 1 mg, e.g., not higher than about 0.7 mg or not higher than about 0.6 mg. Manganese can be provided in any pharmaceutically acceptable form such as, e.g., manganese sulfate and/or an amino acid chelate of manganese. One preferred source of manganese for the purposes of the present invention is manganese gluconate.

If vanadium is to be comprised in a 24-hour dosage unit of the present invention, it is employed in an amount which is usually not lower than about 2 μg, e.g., not lower than about 5 μg or not lower than about 7 μg, but is usually not higher than about 50 μg, e.g., not higher than about 20 μg or not higher than about 15 μg. These amounts also apply if a single 24-hour dosage form unit which comprises vanadium is to be provided. If four dosage form units with identical amounts of vanadium are to be provided to make up a 24-hour dosage unit, vanadium is present in each of these dosage form units in an amount which is usually not lower than about 1 μg, e.g., not lower than about 1.5 μg or not lower than about 2 μg, but is usually not higher than about 8 μg, e.g., not higher than about 4 μg or not higher than about 3 μg. Vanadium can be provided in any pharmaceutically acceptable form such as, e.g., vanadyl sulfate. One preferred source of vanadium for the purposes of the present invention is vanadium citrate.

If molybdenum is to be comprised in a 24-hour dosage unit of the present invention, it is employed in an amount which is usually not lower than about 15 μg, e.g., not lower than about 25 μg or not lower than about 35 μg, but is usually not higher than about 1.5 mg, e.g., not higher than about 0.1 mg or not higher than about 70 μg. These amounts also apply if a single 24-hour dosage form unit which comprises molybdenum is to be provided. If four dosage form units with identical amounts of molybdenum are to be provided to make up a 24-hour dosage unit, molybdenum is present in each of these dosage form units in an amount which is usually not lower than about 7 μg, e.g., not lower than about 10 μg or not lower than about 12 μg, but is usually not higher than about 0.04 mg, e.g., not higher than about 25 μg or not higher than about 18 μg. Molybdenum can be provided in any pharmaceutically acceptable form such as, e.g., sodium molybdate and/or a molybdenum aminoate. One preferred source of molybdenum for the purposes of the present invention is a molybdenum amino acid chelate.

If copper is to be comprised in a 24-hour dosage unit of the present invention, it is employed in an amount which is usually not lower than about 0.5 mg, e.g., not lower than about 1 mg or not lower than about 1.5 mg, but is usually not higher than about 10 mg, e.g., not higher than about 8 mg or not higher than about 5 mg. These amounts also apply if a single 24-hour dosage form unit which comprises copper is to be provided. If four dosage form units with identical amounts of copper are to be provided to make up a 24-hour dosage unit, copper is present in each of these dosage form units in an amount which is usually not lower than about 0.3 mg, e.g., not lower than about 0.5 mg or not lower than about 0.6 mg, but is usually not higher than about 2 mg, e.g., not higher than about 1 mg or not higher than about 0.8 mg. Copper can be provided in any pharmaceutically acceptable form such as, e.g., one or more of cupric oxide, cupric sulfate, cupric gluconate and a copper amino acid chelate. One preferred source of copper for the purposes of the present invention is copper gluconate.

In a preferred method of the present invention for the prevention or alleviation of cardiovascular diseases a subject in need thereof is directed to ingest at least, over a 24 hour period, from about 2.5 mg to about 3.5 mg (e.g., about 3 mg) of vitamin $B_2$, from about 3.5 mg to about 4.5 mg (e.g., about 4 mg) of vitamin $B_6$, from about 700 μg to about 850 μg (e.g., about 800 μg) of vitamin $B_9$, from about 450 μg to about 550 μg (e.g., about 500 μg) of vitamin $B_{12}$, from about 200 mg to about 400 mg (e.g., about 300 mg) of vitamin C, from about 500 IU to about 850 IU (e.g., about 650 IU) of vitamin D, from about 400 IU to about 650 IU (e.g., about 500 IU) of vitamin E, from about 180 μg to about 220 μg (e.g., about 200 μg) of vitamin K, from about 700 mg to about 800 mg (e.g., about 750 mg) of calcium, from about 80 mg to about 120 mg (e.g., about 100 mg) of magnesium, from about 12 mg to about 18 mg (e.g., about 15 mg) of zinc, from about 2.5 mg to about 3.5 mg (e.g., about 3 mg) of boron, from about 150 μg to about 250 μg (e.g., about 200 μg) of chromium, from about 100 μg to about 220 μg (e.g. about 180 μg) of selenium and from about 500 μg to about 800 μg (e.g., about 650 μg) of copper. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of cognitive impairment a subject in need thereof is directed to ingest at least, over a 24 hour period, from about 1400 to about 2000 IU (e.g., about 1700 IU) of vitamin A, from about 2.5 mg to about 3.5 mg (e.g., about 3 mg) of vitamin $B_2$, from about 3.5 mg to about 4.5 mg (e.g., about 4 mg) of vitamin $B_6$, from about 700 μg to about 850 μg (e.g., about 800 μg) of vitamin $B_9$, from about 450 μg to about 550 μg (e.g., about 500 μg) of vitamin $B_{12}$, from about 200 mg to about 400 mg (e.g., about 300 mg) of vitamin C, from about 400 IU to about 650 IU (e.g., about 500 IU) of vitamin E, from about 180 μg to about 220 μg (e.g., about 200 μg) of vitamin K, from about 80 mg to about 120 mg (e.g., about 100 mg) of magnesium, from about 12 mg to about 18 mg (e.g., about 15 mg) of zinc, from about 2.5 mg to about 3.5 mg (e.g., about 3 mg) of boron, from about 120 μg to about 200 μg (e.g., 160 μg) of iodine, from about 100 μg to about 220 μg (e.g. about 180 μg) of selenium and from about 1.8 mg to about 2.5 mg (e.g., about 2.1 mg) of manganese. These 24-hour amounts may be supplied in a single dosage form unit (e.g., a tablet or a capsule) but are preferably supplied in multiple (e.g., two or three preferably identical) dosage form units.

In a preferred method of the present invention for the prevention or treatment of cancer a subject in need thereof is directed to ingest at least, over a 24 hour period, from about 3.5 mg to about 4.5 mg (e.g., about 4 mg) of vitamin $B_6$, from about 700 μg to about 850 μg (e.g., about 800 μg) of vitamin $B_9$, from about 450 μg to about 550 μg (e.g., about 500 μg) of vitamin $B_{12}$, from about 200 mg to about 400 mg (e.g., about 300 mg) of vitamin C, from about 500 IU to about 850 IU (e.g., about 650 IU) of vitamin D, from about 400 IU to about 650 IU (e.g., about 500 IU) of vitamin E, from about 700 mg to about 800 mg (e.g., about 750 mg) of calcium, from about 80 mg to about 120 mg (e.g., about 100 mg) of magnesium, from about 12 mg to about 18 mg (e.g., about 15 mg) of zinc, from about 2.5 mg to about 3.5 mg (e.g., about 3 mg) of boron, from about 500 μg to about 800 μg (e.g., about 650 μg) of copper, from about 100 μg to about 220 μg (e.g. about 180 μg) of selenium, from about 18 mg to about 22 mg (e.g., about 20 mg) of vitamin $B_3$, from about 8 mg to about 12 mg (e.g., about 10 mg) of lutein and from about 300 μg to about 0.5 mg (e.g., about 0.4 mg) of lycopene. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of depression and/or fatigue and/or loss of energy a subject in need thereof is directed to ingest at least, over a 24 hour period, from about 2.5 mg to about 3.5 mg (e.g., about 3 mg) of vitamin $B_2$, from about 3.5 mg to about 4.5 mg (e.g., about 4 mg) of vitamin $B_6$, from about 700 μg to about 850 μg (e.g., about 800 μg) of vitamin $B_9$, from about 450 μg to about 550 μg (e.g., about 500 μg) of vitamin $B_{12}$, from about 200 mg to about 400 mg (e.g., about 300 mg) of vitamin C, from about 500 IU to about 850 IU (e.g., about 650 IU) of vitamin D, from about 700 mg to about 800 mg (e.g., about 750 mg) of calcium, from about 80 mg to about 120 mg (e.g., about 100 mg) of magnesium, from about 2.5 mg to about 3.5 mg (e.g., about 3 mg) of boron and from about 500 μg to about 800 μg (e.g., about 650 μg) of copper. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of a loss of immune function a subject in need thereof is directed to ingest at least, over a 24 hour period, from about 1400 to about 2000 IU (e.g., about 1700 IU) of vitamin A, from about 2.5 mg to about 3.5 mg (e.g., about 3 mg) of vitamin $B_2$, from about 3.5 mg to about 4.5 mg (e.g., about 4 mg) of vitamin $B_6$, from about 500 IU to about 850 IU (e.g., about 650 IU) of vitamin D, from about 400 IU to about 650 IU (e.g., about 500 IU) of vitamin E, from about 180 μg to about 220 μg (e.g., about 200 μg) of vitamin K, from about 12 mg to about 18 mg (e.g., about 15 mg) of zinc, from about 2.5 mg to about 3.5 mg (e.g., about 3 mg) of boron, from about 100 μg to about 220 μg (e.g. about 180 μg) of selenium and from about 500 μg to about 800 μg (e.g., about 650 μg) of copper. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of metabolic syndrome a subject in need thereof is directed to ingest at least, over a 24 hour period, from about 200 mg to about 400 mg (e.g., about 300 mg) of vitamin C, from about 500 IU to about 850 IU (e.g., about 650 IU) of vitamin D, from about 400 IU to about 650 IU (e.g., about 500 IU) of vitamin E, from about 20 μg to about 50 μg (e.g., about 35 μg) of vitamin $B_7$, from about 80 mg to about 120 mg (e.g., about 100 mg) of magnesium, from about 12 mg to about 18 mg (e.g., about 15 mg) of zinc, from about 1.8 mg to about 2.5 mg (e.g., about 2.1 mg) of manganese and from about 150 µg to about 250 µg (e.g., about 200 µg) of chromium. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of osteopenia a subject in need thereof is directed to ingest at least, over a 24 hour period, from about 1400 to about 2000 IU (e.g., about 1700 IU) of vitamin A, from about 500 IU to about 850 IU (e.g., about 650 IU) of vitamin D, from about 180 µg to about 220 µg (e.g., about 200 µg) of vitamin K, from about 700 mg to about 800 mg (e.g., about 750 mg) of calcium, from about 80 mg to about 120 mg (e.g., about 100 mg) of magnesium, from about 12 mg to about 18 mg (e.g., about 15 mg) of zinc, from about 2.5 mg to about 3.5 mg (e.g., about 3 mg) of boron, from about 1.8 mg to about 2.5 mg (e.g., about 2.1 mg) of manganese and from about 500 µg to about 800 µg (e.g., about 650 µg) of copper. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of arthritis a subject in need thereof is directed to ingest at least, over a 24 hour period, from about 2.5 mg to about 3.5 mg (e.g., about 3 mg) of vitamin $B_2$, from about 500 IU to about 850 IU (e.g., about 650 IU) of vitamin D, from about 80 mg to about 120 mg (e.g., about 100 mg) of magnesium, from about 2.5 mg to about 3.5 mg (e.g., about 3 mg) of boron and from about 500 µg to about 800 µg (e.g., about 650 µg) of copper. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of muscle weakness a subject in need thereof is directed to ingest at least, over a 24 hour period, from about 700 µg to about 850 µg (e.g., about 800 µg) of vitamin $B_9$, from about 450 µg to about 550 µg (e.g., about 500 µg) of vitamin $B_{12}$, from about 500 IU to about 850 IU (e.g., about 650 IU) of vitamin D, from about 400 IU to about 650 IU (e.g., about 500 IU) of vitamin E, from about 180 µg to about 220 µg (e.g., about 200 µg) of vitamin K, from about 700 mg to about 800 mg (e.g., about 750 mg) of calcium, from about 80 mg to about 120 mg (e.g., about 100 mg) of magnesium, from about 12 mg to about 18 mg (e.g., about 15 mg) of zinc and from about 2.5 mg to about 3.5 mg (e.g., about 3 mg) of boron. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of obesity a subject in need thereof is directed to ingest at least, over a 24 hour period, from about 500 IU to about 850 IU (e.g., about 650 IU) of vitamin D, from about 700 mg to about 800 mg (e.g., about 750 mg) of calcium, from about 80 mg to about 120 mg (e.g., about 100 mg) of magnesium and from about 2.5 mg to about 3.5 mg (e.g., about 3 mg) of boron. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of inflammatory processes a subject in need thereof is directed to ingest at least, over a 24 hour period, from about 400 IU to about 650 IU (e.g., about 500 IU) of vitamin E, from about 180 µg to about 220 µg (e.g., about 200 µg) of vitamin K, from about 12 mg to about 18 mg (e.g., about 15 mg) of zinc and from about 2.5 mg to about 3.5 mg (e.g., about 3 mg) of boron. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of oxidative stress a subject in need thereof is directed to ingest at least, over a 24 hour period, from about 1.5 mg to about 2.5 mg (e.g., about 2 mg) of vitamin $B_1$, from about 2.5 mg to about 3.5 mg (e.g., about 3 mg) of vitamin $B_2$, from about 18 mg to about 22 mg (e.g., about 20 mg) of vitamin $B_3$, from about 3.5 mg to about 4.5 mg (e.g., about 4 mg) of vitamin $B_6$, from about 200 mg to about 400 mg (e.g., about 300 mg) of vitamin C, from about 400 IU to about 650 IU (e.g., about 500 IU) of vitamin E, from about 180 µg to about 220 µg (e.g., about 200 µg) of vitamin K, from about 80 mg to about 120 mg (e.g., about 100 mg) of magnesium, from about 12 mg to about 18 mg (e.g., about 15 mg) of zinc, from about 100 µg to about 220 µg (e.g. about 180 µg) of selenium, from about 500 µg to about 800 µg (e.g., about 650 µg) of copper and from about 1.8 mg to about 2.5 mg (e.g., about 2.1 mg) of manganese. These 24-hour amounts may be supplied in a single dosage form unit (e.g., a tablet or a capsule) but are preferably supplied in multiple (e.g., two or three preferably identical) dosage form units.

In a preferred method of the present invention for promoting wound healing a subject in need thereof is directed to ingest at least, over a 24 hour period, from about 700 mg to about 800 mg (e.g., about 750 mg) of calcium, from about 80 mg to about 120 mg (e.g., about 100 mg) of magnesium, from about 500 µg to about 800 µg (e.g., about 650 µg) of copper and from about 1.8 mg to about 2.5 mg (e.g., about 2.1 mg) of manganese. These 24-hour amounts may be supplied in a single dosage form unit (e.g., a tablet or a capsule) but are preferably supplied in multiple (e.g., two or three preferably identical) dosage form units.

In a preferred method of the present invention for the prevention or alleviation of impaired vision a subject in need thereof is directed to ingest at least, over a 24 hour period, from about 1400 to about 2000 IU (e.g., about 1700 IU) of vitamin A, from about 2.5 mg to about 3.5 mg (e.g., about 3 mg) of vitamin $B_2$, from about 3.5 mg to about 4.5 mg (e.g., about 4 mg) of vitamin $B_6$, from about 700 µg to about 850 µg (e.g., about 800 µg) of vitamin $B_9$, from about 450 µg to about 550 µg (e.g., about 500 µg) of vitamin $B_{12}$, from about 200 mg to about 400 mg (e.g., about 300 mg) of vitamin C, from about 500 IU to about 850 IU (e.g., about 650 IU) of vitamin D, from about 400 IU to about 650 IU (e.g., about 500 IU) of vitamin E, from about 700 mg to about 800 mg (e.g., about 750 mg) of calcium, from about 80 mg to about 120 mg (e.g., about 100 mg) of magnesium, from about 12 mg to about 18 mg (e.g., about 15 mg) of zinc, from about 2.5 mg to about 3.5 mg (e.g., about 3 mg) of boron, from about 8 mg to about 12 mg (e.g., about 10 mg) of lutein and from about 8 mg to about 12 mg (e.g., about 10 mg) of zeaxanthin and, optionally, from about 300 µg to about 0.5 mg (e.g., about 0.4 mg) of lycopene. These 24-hour amounts may be supplied in a single dosage form unit (e.g., a tablet or a capsule) but are preferably supplied in multiple (e.g., two or three preferably identical) dosage form units.

The dosage form units of the present invention can be manufactured by processes which are well known to those of skill in the art. For example, for the manufacture of tablets, the micronutrients may be dispersed uniformly into a mixture of excipients, for example, by high shear granulation, low shear granulation, fluid bed granulation, or by blending for direct compression. Excipients may include diluents, binders, disintegrants, dispersants, lubricants, glidants, stabilizers, surfactants and colorants. Diluents, also termed "fillers", are typically used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Apparently, some of these fillers may also be used as sources for minerals which are used in this invention. Binders impart cohesive qualities to a tablet formulation and are used to ensure that a tablet remains intact after compression. Non-limiting examples of suitable binders include starch (including corn starch and pregelatinized starch), gelatin, sugars (e.g., glucose, dextrose, sucrose, lactose, mannitol and sorbitol), celluloses, polyethylene glycol, waxes, natural and synthetic gums, e.g., guar gum, acacia, tragacanth, sodium alginate, and synthetic polymers such as polymethacrylates and polyvinylpyrrolidone. Lubricants facilitate tablet manufacture; non-limiting examples thereof include magnesium stearate, calcium stearate, stearic acid and polyethylene glycol. Disintegrants facilitate tablet disintegration after administration, and non-limiting examples thereof include starches, alginic acid, cross-linked polymers such as, e.g., cross-linked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers inhibit or retard drug decomposition reactions, including oxidative reactions. Surfactants may be anionic, cationic, amphoteric or nonionic. If desired, the dosage form units may also contain minor amounts of nontoxic auxiliary substances such as pH buffering agents, preservatives, e.g., antioxidants, wetting or emulsifying agents, solubilizing agents, coating agents, flavoring agents, and the like.

Extended/sustained release formulations may be made by choosing the right combination of excipients that slow the release of the active ingredients by coating or temporarily bonding or decreasing the solubility of the micronutrients employed. Examples of these excipients include cellulose ethers such as hydroxypropylmethylcellulose (e.g., Methocel K4M), polyvinylacetate-based excipients such as, e.g., Kollidon SR, and polymers and copolymers based on methacrylates and methacrylic acid such as, e.g., Eudragit NE 30D.

Of course, one or more micronutrients or other physiologically active substances which are different from those mentioned above may also be present in a dosage (form) unit of the present invention. Non-limiting examples of corresponding micronutrients (which may be employed, for example, in amounts which are commonly used for these micronutrients) include the following: essential and non-essential amino acids (preferably in the L-form) and derivatives (e.g., N-acetyl derivatives) thereof such as, e.g., arginine, carnitine, acetyl-carnitine, ornithine, GABA, glutamine, glutathione, glycine, lysine, cysteine, N-acetyl-cysteine, homocysteine, methionine, choline, serine, theanine, phosphatidylserine, tyrosine, and taurine; antioxidants such as, e.g., coenzyme Q10, DHEA, policosanol, bioflavonoids such as, e.g., curcumin, epicatechin, epigallocatechin, tangeritin, hesperidin, quercitin, rutin, and resveratrol, silymarin, MSM, melatononin, beta-sitosterol, SOD and plant extracts such as, e.g., ginkgo biloba, St. John's Wort, blueberry extract, pomegranate extract, saw palmetto.

Example

A dosage form unit (recommended intake per 24 hour period: 4 units) is prepared in the form of a tablet or capsule which comprises the following micronutrients:

| Vitamin A | 750 IU | e.g., 50% retinol palmitate and 50% beta-carotene |
|---|---|---|
| Vitamin C | 100 mg | |
| Vitamin E | 100 IU | e.g., as d-alpha tocopheryl succinate |
| Calcium | 190 mg | e.g., as calcium carbonate |
| Zinc | 10 mg | e.g., as zinc oxide |
| Copper | 0.7 mg | e.g., as copper gluconate |
| Folic Acid | 200 mcg | |
| Magnesium | 25 mg | e.g., as magnesium oxide |
| Niacin | 5 mg | |
| Riboflavin | 1 mg | |
| Vitamin $B_6$ | 1 mg | e.g., as pyridoxine hydrochloride |
| Vitamin $B_{12}$ | 125 mcg | |
| Boron | 0.8 mg | e.g., as boron amino acid chelate |
| Chromium | 50 mcg | e.g., as chromium amino acid chelate |
| Lutein | 1.5 mg | |
| Zeaxanthin | 2.5 mg | |
| Vitamin D | 200 IU | e.g., as vitamin $D_3$ |
| Nickel | 40 mcg | e.g., as nickel amino acid chelate |
| Silicon | 1.5 mg | |
| Selenium | 50 mcg | e.g., as sodium selenite |
| Vitamin K | 30 mcg | |
| Biotin | 20 mcg | |
| Iodine | 30 mcg | e.g., as potassium iodide |
| Lycopene | 1.5 mg | |
| Manganese | 0.5 mg | e.g., as manganese gluconate |
| Molybdenum | 15 mcg | e.g., as molybdenum amino acid chelate |
| Pantothenic Acid | 2 mg | e.g., as d-calcium pantothenate |
| Thiamine | 0.5 mg | e.g., as thiamine hydrochloride |
| Vanadium | 2.5 mcg | e.g., as vanadium citrate |

It is noted that the foregoing example has been provided merely for the purpose of explanation and is in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A micronutrient dosage unit for ingestion by a human over a period of about 24 hours, wherein the dosage unit comprises magnesium, boron, vitamin D, vitamin $B_9$, and vitamin $B_{12}$, and wherein the dosage unit comprises:
    (i) from about 20 mg to about 40 mg of magnesium per 1 mg of boron;
    (ii) from about 0.9 mg to about 1.6 mg of magnesium per 10 IU of vitamin D;
    (iii) from about 1.2 µg to about 1.9 µg of vitamin $B_9$ per 1 µg of vitamin $B_{12}$; and
    (iv) from about 20 µg to about 60 µg of boron per 10 IU of vitamin D.

2. The dosage unit of claim 1, wherein the dosage unit comprises from about 25 mg to about 35 mg of magnesium per 1 mg of boron.

3. The dosage unit of claim 1, wherein the dosage unit comprises from about 1.0 mg to about 1.5 mg of magnesium per 10 IU of vitamin D.

4. The dosage unit of claim 1, wherein the dosage unit comprises from about 1.25 µg to about 1.8 µg of vitamin $B_9$ per 1 µg of vitamin $B_{12}$.

5. The dosage unit of claim 1, wherein the dosage unit comprises from about 25 µg to about 55 µg of boron per 10 IU of vitamin D.

6. The dosage unit of claim 1, wherein the dosage unit comprises
(i') from about 25 mg to about 35 mg of magnesium per 1 mg of boron;
(ii') from about 1.0 mg to about 1.5 mg of magnesium per 10 IU of vitamin D;
(iii') from about 1.25 µg to about 1.8 µg of vitamin $B_9$ per 1 µg of vitamin $B_{12}$; and
(iv') from about 25 µg to about 55 µg of boron per 10 IU of vitamin D.

7. The dosage unit of claim 6, wherein the dosage unit comprises from about 28 mg to about 33 mg of magnesium per 1 mg of boron.

8. The dosage unit of claim 6, wherein the dosage unit comprises from about 1.1 mg to about 1.4 mg of magnesium per 10 IU of vitamin D.

9. The dosage unit of claim 6, wherein the dosage unit comprises from about 1.3 µg to about 1.7 µg of vitamin $B_9$ per 1 µg of vitamin $B_{12}$.

10. The dosage unit of claim 6, wherein the dosage unit comprises from about 30 µg to about 50 µg of boron per 10 IU of vitamin D.

11. The dosage unit of claim 6, wherein the dosage unit comprises
(i") from about 28 mg to about 33 mg of magnesium per 1 mg of boron;
(ii") from about 1.1 mg to about 1.4 mg of magnesium per 10 IU of vitamin D;
(iii") from about 1.3 µg to about 1.7 µg of vitamin $B_9$ per 1 µg of vitamin $B_{12}$; and
(iv") from about 30 µg to about 50 µg of boron per 10 IU of vitamin D.

12. The dosage unit of claim 1, wherein the dosage unit comprises from about 250 µg to about 750 µg of vitamin $B_{12}$ and from about 50 mg to about 150 mg of magnesium.

13. The dosage unit of claim 2, wherein the dosage unit comprises from about 250 µg to about 750 µg of vitamin $B_{12}$ and from about 50 mg to about 150 mg of magnesium.

14. The dosage unit of claim 3, wherein the dosage unit comprises from about 250 µg to about 750 µg of vitamin $B_{12}$ and from about 50 mg to about 150 mg of magnesium.

15. The dosage unit of claim 4, wherein the dosage unit comprises from about 250 µg to about 750 µg of vitamin $B_{12}$ and from about 50 mg to about 150 mg of magnesium.

16. The dosage unit of claim 5, wherein the dosage unit comprises from about 250 µg to about 750 µg of vitamin $B_{12}$ and from about 50 mg to about 150 mg of magnesium.

17. The dosage unit of claim 6, wherein the dosage unit comprises from about 250 µg to about 750 µg of vitamin $B_{12}$ and from about 50 mg to about 150 mg of magnesium.

18. The dosage unit of claim 6, wherein the dosage unit comprises from about 350 µg to about 700 µg of vitamin $B_{12}$ and from about 70 mg to about 130 mg of magnesium.

19. The dosage unit of claim 7, wherein the dosage unit comprises from about 350 µg to about 700 µg of vitamin $B_{12}$ and from about 70 mg to about 130 mg of magnesium.

20. The dosage unit of claim 8, wherein the dosage unit comprises from about 350 µg to about 700 µg of vitamin $B_{12}$ and from about 70 mg to about 130 mg of magnesium.

21. The dosage unit of claim 9, wherein the dosage unit comprises from about 350 µg to about 700 µg of vitamin $B_{12}$ and from about 70 mg to about 130 mg of magnesium.

22. The dosage unit of claim 10, wherein the dosage unit comprises from about 350 µg to about 700 µg of vitamin $B_{12}$ and from about 70 mg to about 130 mg of magnesium.

23. The dosage unit of claim 11, wherein the dosage unit comprises from about 350 µg to about 700 µg of vitamin $B_{12}$ and from about 70 mg to about 130 mg of magnesium.

24. The dosage unit of claim 11, wherein the dosage unit comprises from about 500 µg to about 650 µg of vitamin $B_{12}$ and from about 70 mg to about 130 mg of magnesium.

25. The dosage unit of claim 1, wherein the vitamin D comprises vitamin $D_3$.

26. The dosage unit of claim 6, wherein the vitamin D comprises vitamin $D_3$.

27. The dosage unit of claim 11, wherein the wherein the vitamin D comprises vitamin $D_3$.

28. The dosage unit of claim 24, wherein the vitamin D comprises vitamin $D_3$.

29. The dosage unit of claim 1, wherein the dosage unit is substantially free of iron.

30. The dosage unit of claim 6, wherein the dosage unit is substantially free of iron and phosphorus.

31. The dosage unit of claim 11, wherein the dosage unit is substantially free of iron and phosphorus.

32. The dosage unit of claim 24, wherein the dosage unit is substantially free of iron.

33. The dosage unit of claim 1, wherein the dosage unit further comprises one or more of the following:
(v) from about 5 IU to about 50 IU of vitamin E per 1 mg of zinc;
(vi) from about 0.7 mg to about 1.5 mg of vitamin $B_6$ per 1 mg of vitamin $B_2$;
(vii) from about 2.5 IU to about 3.6 IU of vitamin E per 1 µg of vitamin K;
(viii) from about 8 mg to about 12 mg of calcium per 10 IU of vitamin D;
(ix) from about 5 mg to about 10 mg of calcium per 1 mg of magnesium;
(x) from about 25 IU to about 50 IU of vitamin A per 10 IU of vitamin D;
(xi) from about 50 IU to about 100 IU of vitamin A per 1 mg of Zn;
(xii) from about 3 IU to about 10 IU of vitamin A per 1 IU of vitamin E;
(xiii) from about 15 IU to about 30 IU of vitamin A per 1 µg of vitamin K;
(xiv) from about 0.1 µg to about 0.8 µg of chromium per 1 mg of vitamin C; and
(xv) from about 3.5 mg to about 6.5 mg of vitamin $B_6$ per 1 mg of vitamin $B_9$.

34. The dosage unit of claim 6, wherein the dosage unit further comprises two or more of the following:
(v') from about 7 IU to about 30 IU of vitamin E per 1 mg of zinc;
(vi') from about 0.8 mg to about 1.3 mg of vitamin $B_6$ per 1 mg of vitamin $B_2$;
(vii') from about 2.8 IU to about 3.5 IU of vitamin E per 1 µg of vitamin K;
(viii') from about 9 mg to about 10 mg of calcium per 10 IU of vitamin D;
(ix') from about 6 mg to about 9 mg of calcium per 1 mg of magnesium;

(x') from about 30 IU to about 45 IU of vitamin A per 10 IU of vitamin D;
(xi') from about 60 IU to about 90 IU of vitamin A per 1 mg of Zn;
(xii') from about 5 IU to about 9 IU of vitamin A per 1 IU of vitamin E;
(xiii') from about 20 IU to about 28 IU of vitamin A per 1 μg of vitamin K;
(xiv') from about 0.2 μg to about 0.7 μg of chromium per 1 mg of vitamin C; and
(xv') from about 4 mg to about 6 mg of vitamin $B_6$ per 1 mg of vitamin $B_9$.

35. The dosage unit of claim 11, wherein the dosage unit further comprises:
(v") from about 8 IU to about 15 IU of vitamin E per 1 mg of zinc;
(vi") from about 0.9 mg to about 1.2 mg of vitamin $B_6$ per 1 mg of vitamin $B_2$;
(vii") from about 3.0 IU to about 3.4 IU of vitamin E per 1 μg of vitamin K;
(viii") from about 9.2 mg to about 9.7 mg of calcium per 10 IU of vitamin D;
(ix") from about 7 mg to about 8.5 mg of calcium per 1 mg of magnesium;
(x") from about 33 IU to about 40 IU of vitamin A per 10 IU of vitamin D;
(xi") from about 70 IU to about 80 IU of vitamin A per 1 mg of Zn;
(xii") from about 6.5 IU to about 10 IU of vitamin A per 1 IU of vitamin E;
(xiii") from about 24 IU to about 26 IU of vitamin A per 1 μg of vitamin K;
(xiv") from about 0.3 μg to about 0.6 μg of chromium per 1 mg of vitamin C; and
(xv") from about 4.5 mg to about 5.5 mg of vitamin $B_6$ per 1 mg of vitamin $B_9$.

36. The dosage unit of claim 35, wherein the dosage unit is substantially free of iron.

37. A solid micronutrient dosage form unit which is administerable to a human, wherein the dosage form unit comprises magnesium, boron, vitamin D, vitamin $B_9$, and vitamin $B_{12}$, and wherein the dosage form unit comprises:
(i) from about 20 mg to about 40 mg of magnesium per 1 mg of boron;
(ii) from about 0.9 mg to about 1.6 mg of magnesium per 10 IU of vitamin D;
(iii) from about 1.2 μg to about 1.9 μg of vitamin $B_9$ per 1 μg of vitamin $B_{12}$; and
(iv) from about 20 μg to about 60 μg of boron per 10 IU of vitamin D.

38. The dosage form unit of claim 37, wherein the dosage form unit is free of iron and comprises one or more of:
(a) from about 150 μg to about 300 μg of vitamin $B_9$
(b) from about 80 μg to about 250 μg of vitamin $B_{12}$
(c) from about 150 IU to about 300 IU of vitamin D
(d) from about 15 mg to about 40 mg of magnesium
(e) from about 0.5 mg to about 1.5 mg of boron.

39. The dosage form unit of claim 37, wherein the dosage form unit is free of iron and comprises:
(a) from about 150 μg to about 300 μg of vitamin $B_9$
(b) from about 80 μg to about 250 μg of vitamin $B_{12}$
(c) from about 150 IU to about 300 IU of vitamin D
(d) from about 15 mg to about 40 mg of magnesium
(e) from about 0.5 mg to about 1.5 mg of boron.

40. The dosage form unit of claim 37, wherein the dosage form unit comprises
(i') from about 25 mg to about 35 mg of magnesium per 1 mg of boron;
(ii') from about 1.0 mg to about 1.5 mg of magnesium per 10 IU of vitamin D;
(iii') from about 1.25 μg to about 1.8 μg of vitamin $B_9$ per 1 μg of vitamin $B_{12}$; and
(iv') from about 25 μg to about 55 μg of boron per 10 IU of vitamin D.

41. The dosage form unit of claim 37, wherein the dosage form unit is free of iron and comprises
(i") from about 28 mg to about 33 mg of magnesium per 1 mg of boron;
(ii") from about 1.1 mg to about 1.4 mg of magnesium per 10 IU of vitamin D;
(iii") from about 1.3 μg to about 1.7 μg of vitamin $B_9$ per 1 μg of vitamin $B_{12}$; and
(iv") from about 30 μg to about 50 μg of boron per 10 IU of vitamin D.

42. The dosage form unit of claim 37, wherein the dosage form unit is in the form of a tablet, a capsule or a caplet.

43. The dosage form unit of claim 38, wherein the dosage form unit is in the form of a tablet, a capsule or a caplet.

44. The dosage form unit of claim 39, wherein the dosage form unit is in the form of a tablet, a capsule or a caplet.

* * * * *